(12) United States Patent
Pekurovsky et al.

(10) Patent No.: US 11,744,915 B2
(45) Date of Patent: Sep. 5, 2023

(54) DIAGNOSTIC DEVICE

(71) Applicant: 3M INNOVATIVE PROPERTIES COMPANY, St. Paul, MN (US)

(72) Inventors: Mikhail L. Pekurovsky, Bloomington, MN (US); Matthew S. Stay, Bloomington, MN (US); Hannah J. Loughlin, Mahtomedi, MN (US); Kevin (Continued)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/906,704

(22) PCT Filed: Mar. 16, 2021

(86) PCT No.: PCT/IB2021/052179
§ 371 (c)(1),
(2) Date: Sep. 19, 2022

(87) PCT Pub. No.: WO2021/198827
PCT Pub. Date: Oct. 7, 2021

(65) Prior Publication Data
US 2023/0120911 A1    Apr. 20, 2023

Related U.S. Application Data

(60) Provisional application No. 63/003,169, filed on Mar. 31, 2020.

(51) Int. Cl.
*A61L 15/58* (2006.01)
*B01L 3/00* (2006.01)

(52) U.S. Cl.
CPC .............. *A61L 15/58* (2013.01); *B01L 3/5023* (2013.01); *B01L 3/502738* (2013.01)

(58) Field of Classification Search
CPC .... A61L 15/58; B01L 3/5023; B01L 3/502738
See application file for complete search history.

(56) References Cited

U.S. PATENT DOCUMENTS

| 8,628,729 B2 | 1/2014 | Carrilho et al. |
| 9,597,684 B2 | 3/2017 | Vella et al. |
| (Continued) | | |

FOREIGN PATENT DOCUMENTS

| EP | 1344059 B1 | 10/2007 |
| WO | 2011094342 A1 | 8/2011 |
| (Continued) | | |

OTHER PUBLICATIONS

AGUIRRE-SOTO, "Excitation of Metastable Intermediates in Organic Photoredox Catalysis: Z-Scheme Approach Decreases Catalyst Inactivation", ACS Catalysis, 2018, Vol. 08, pp. 6394-6400.
(Continued)

*Primary Examiner* — Dennis White
(74) *Attorney, Agent, or Firm* — Thomas M. Spielbauer

(57) ABSTRACT

Diagnostic devices for quantitative or qualitative analysis of a sample fluid including an analyte include at least two portions made from a hydrophilic material. The planar portions are stacked on each other and each occupy a different and substantially parallel plane to form a three-dimensional structure. At least one of the planar portions includes a hydrophobic region formed by applying a low surface energy material that extends through a thickness of the substrate portion from a first major surface to a second major surface thereof. The hydrophilic regions in the overlying substantially parallel substrate portions can be aligned with each other such that a fluid is passively transported between adjacent hydrophilic regions to provide a sample flow path between adjacent substrate portions.

20 Claims, 7 Drawing Sheets

(72) Inventors: T. Reddy, Minneapolis, MN (US); Henrik B. Van Lengerich, St. Paul, MN (US); Ann M. Gilman, Bayport, MN (US); Matthew R.D. Smith, Woodbury, MN (US)

(56) References Cited

U.S. PATENT DOCUMENTS

| 9,669,638 | B2 | 6/2017 | Ferrara, Jr. et al. |
| 2012/0270235 | A1 | 10/2012 | Kim et al. |
| 2015/0355132 | A1* | 12/2015 | Crooks et al. ........ C12Q 1/6813 422/69 |
| 2019/0113512 | A1 | 4/2019 | Sikes Johnson et al. |
| 2020/0057058 | A1 | 2/2020 | Olsen et al. |

FOREIGN PATENT DOCUMENTS

| WO | 2022200866 | A1 | 9/2022 |
| WO | 2022200867 | A1 | 9/2022 |
| WO | 2022200868 | A1 | 9/2022 |
| WO | 2022208321 | A1 | 10/2022 |

OTHER PUBLICATIONS

AGUIRRE-SOTO, "On the role of N-vinylpyrrolidone in the aqueous radical-initiated copolymerization with PEGDA mediated by eosin Y in the presence of O2", Polymer Chemistry, 2019, Vol. 10, No. 8, pp. 926-937.
AZZI, "Diagnostic Salivary Tests for SARS-CoV-2", Journal of Dental Research, 2021, Vol. 100, No. 2, pp. 115-123.
AZZI, "Rapid Salivary Test Suitable for mass screening program to detect SARS-CoV-2: A diagnostic accuracy study". The Journal of Infection, 2020, Vol. 81, No. 3, pp. e75-e78.
AZZI, "Saliva is a reliable tool to detect SARS-CoV-2", Journal of infection, 2020, Vol. 81, pp. e45-e50.
BADU-TAWIAH, "Polymerization-based signal amplification for paper-based immunoassays", Lab on a Chip, 2015, Vol. 15, No. 3, pp. 655-659.
DELLAL, "Low-cost Plug and Play Photochemistry Reactor", HardwareX, 2018, Vol. 03, pp. 1-9.
FERNANDES, "Fabrication of Three-dimensional Paper-Based Microfluidic Devices For Immunoassays", Journal of Visualized Experiments, 2017, Vol, e55287, No. 121, pp. 1-10.
International Search Report for PCT International Application No. PCT/US2021/024280, mailed on Aug. 12, 2021, 4 pages.
KAASTRUP, "Impact of Dissociation Constant on the Detection Sensitivity of Polymerization-Based Signal Amplification Reactions", Analytical Chemistry, 2013, Vol. 85, No. 17, pp. 8055-8060.
KAASTRUP, "Investigation of dendrimers functionalized with eosin as macrophotoinitiators for polymerization-based signal amplification reactions", RSC Advances, 2015, Vol. 05, No. 20, pp. 15652-15659.
KAASTRUP, "Polymerization-based Signal Amplification Under Ambient Conditions with Thirty-Five Second Reaction Times", Lab on a Chip, 2012, Vol. 12, No. 20, pp. 4055-4058.
KAASTRUP, "Using Photo-Initiated Polymerization Reactions To Detect Molecular Recognition", Chemical Society Reviews, 2016, Vol. 45, No. 3, pp. 532-545.
KAASTRUP, "UV-Vis/FT-NIR In-situ monitoring of visible-light induced polymerization of PEGDA hydrogels initiated by eosin/triethanolamine/O2", Polymer Chemistry, 2016, Vol. 07, No. 3, pp. 592-602.

KIM, "A SARS-CoV-2 Antigen Test Using Engineered Affinity Proteins", 2021, PP. S-1-S-30.
LATHWAL, "A method for Designing Instrument-Free, Quantitative Immunoessays," Analytical Chemistry, 2018, Vol. 88, No. 6, pp. 3194-3202.
LATHWAL, "Assessment Of Colorimetric Amplification Methods In A Paper-Based Immunoassay For Diagnosis Of Malaria", Lab on a Chip, 2016, Vol. 16, No. 8, pp. 1374-1382.
LEE, "Balancing the Initiation and Molecular Recognition Capabilities of Eosin Macroinitiators of Polymerization-Based Signal Amplification Reactions", Macromolecular Rapid communications, 2014, Vol. 35, No. 10, pp. 981-986.
LEE, "Systematic Study of Fluorescein-Functionalized Macrophotoinitiators for Colorimetric Bioassays", 2012, Vol. 13, No. 4, pp. 1136-1143.
MILLER, "Activity-Based Assessment Of An Engineered Hyperthermophilic Protein As A Capture Agent In Paper-Based Diagnostic Tests", Molecular Systems Design & Engineering, 2016, Vol. 01, pp. 377-381.
MILLER, "Addressing barriers to the development and adoption of rapid diagnostic tests in global health", Nanobiomedicine, 2015, Vol. 02, pp. 1-21.
MILLER, "Paper-Based Diagnostics in The Antigen-Depletion Regime: High Density Immobilization Of rcSso7d-Cellulose Binding Domain Fusion Proteins For Efficient Target Capture", Biosensors and Bioelectronics, 2018, Vol. 102, pp. 456-463,.
REBOUND, "From Paper-based microfluidics for DNA diagnostics of Malaria in Low Resource Underserved Rural Communities", 2019, Vol. 116, No.11, pp. 4834-4842.
REECE, "Staged Inertial Microfluidic Focusing for Complex Fluid Enrichment", RCS Advances, 2015, Vol. 15, No. 6, pp. 53857-53864.
SHATOVA, "Portable, Constriction-Expansion Blood Plasma Separation and Polymerization-Based Malaria Detection", Analytical Chemistry, 2018, Vol. 88, No. 15, pp. 7627-7632.
SUNG, "Engineering Hyperthermostable rcSso7d as Reporter Molecule for In Vitro Diagnostic Tests", 2018, Molecular Systems Design & Engineering, 2018, Vol. 03, pp. 877-882.
WASHBURN, "The Dynamics of Capillary Flow", Physical Review, 1921, Vol. 17, No. 3, pp. 273-283.
WELCH, "Analysis of Inactivation of SARS-CoV-2 by Specimen Transport Media, Nucleic Acid Extraction Reagents, Detergents, and Fixatives", Journal of Clinical Microbiology, 2020, Vol. 58, No. 11, pp. e01716-e01720.
WONG, "A Quantitative Analysis of peroxy- mediated cyclic regeneration of eosin in oxygen-rich photopolymerization conditions", Polymer, 2015, Vol. 69, pp. 169-177.
WONG, "The impact of continuous oxygen flux in a thin film photopolymerization reaction with peroxy-mediated regeneration of initiator", Macromolecular Theory And Simulations, 2016, Vol. 25, No. 3, pp. 229-237.
XU, "Paper-Origami-Based Multiplexed Malaria Diagnostics from Whole Blood", Angewandte Chemie (International Edition), 2016, Vol. 55, No. 49, pp. 15250-15253.
YEE, "Detection of Biomarkers of Periodontal Disease in Human Saliva Using Stabilized, Vertical Flow Immunoassays", ACS Sensors, 2017, Vol. 02, No. 11, pp. 1589-1593.
YETISEN, "Paper-based Microfluidic Point-of-Care Diagnostic Devices", Lab Chip, 2013, Vol. 13, No. 12, pp. 2210-2251.

* cited by examiner

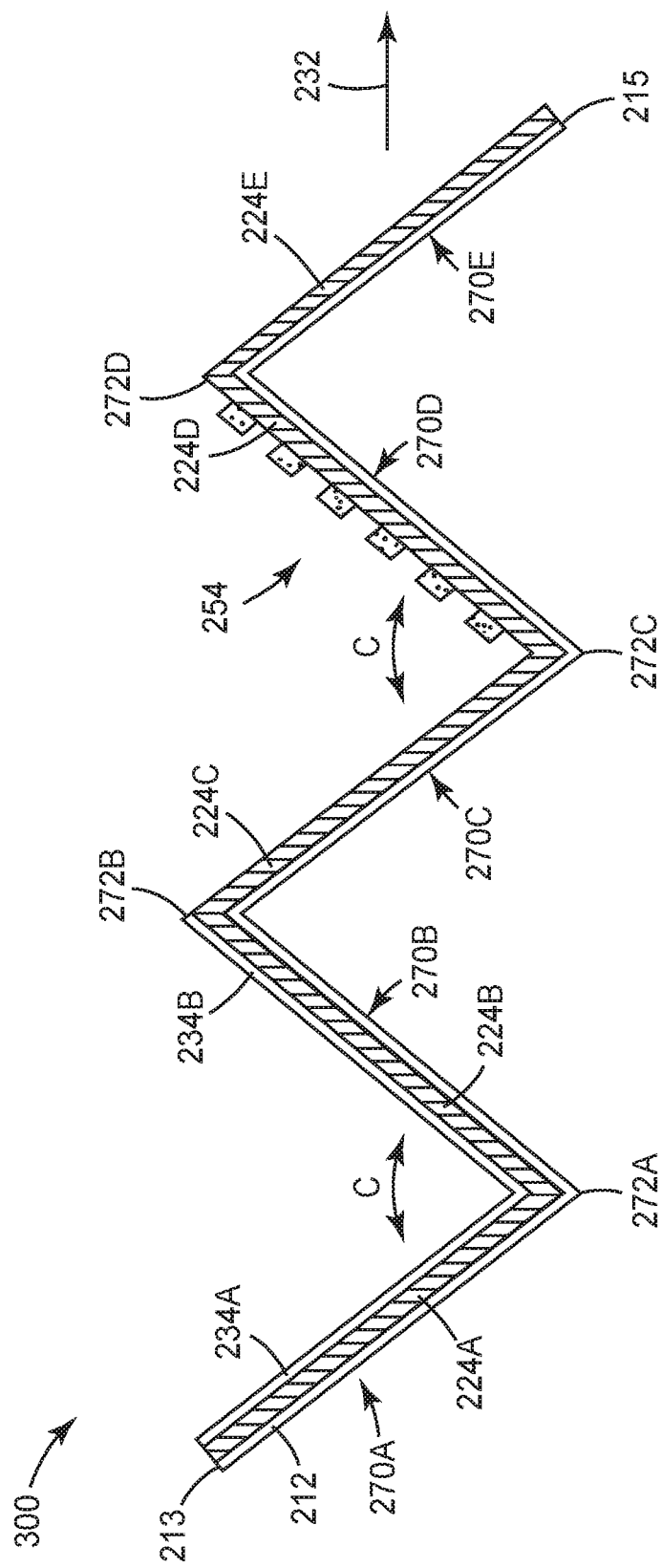

DIAGNOSTIC DEVICE

CROSS REFERENCE TO RELATED APPLICATIONS

This application is a national stage filing under 35 U.S.C. of PCT/IB2021/052179, filed Mar. 06, 2021, which claims the benefit of US Application No. 63/003,169, filed Mar. 31, 2020, the disclosure of which is incorporated by reference in its/their entirety herein.

BACKGROUND

Simple, low-cost diagnostic technologies are an important component of strategies for improving healthcare and access to healthcare in developing nations and resource-limited settings. According to the World Health Organization, diagnostic devices for use in developing countries should be ASSURED (affordable, sensitive, specific, user-friendly, rapid and robust, equipment-free, and deliverable to end users).

Inexpensive, portable, and easy-to-use diagnostic devices have used a porous substrate including a reagent selected to rapidly perform quantitative or qualitative analysis of a fluid sample such as, for example, a bodily fluid, an industrial fluid, or water, in the field when laboratory facilities are not available or easily accessed for sample analysis. In one example, a paper-based diagnostic device includes a colorimetric immunoassay reagent with a color change as a readout, and the color change readout can be detected visually or with a machine to provide a rapid, low-cost diagnosis of the presence of an infectious disease. In various examples, analytes in a sample can be rapidly detected using the diagnostic devices include viral antigens, bacterial antigens, fungal antigens, parasitic antigens, cancer antigens, metabolic markers, and combinations thereof. In one example, in an immunochromatographic diagnostic assay, antibodies acting as binding proteins can be used to capture disease-relevant biomarkers from the patient sample, and then produce a visible diagnostic signal resulting from the binding event.

In some examples, the diagnostic devices include multiple layers of a porous material disposed in planes parallel to one another and in face-to-face contact. The various layers of the diagnostic device include fluid impermeable hydrophobic regions and hydrophilic water absorbent regions arranged to provide a sample flow path configured such that a fluid sample can wick or flow from one layer to another. At least some of the layers include reagents, buffer salts, analytes (for example antigens) and binders (for example, antibodies) selected to perform a multiplexed assay.

To manufacture a diagnostic device including multiple planar regions having different reagents or different patterns of hydrophobic and hydrophilic regions, multiple layers must be individually produced, accurately stacked and aligned to provide the sample flow path, and adhered to maintain the continuity of the sample flow path and form an operable stack. In practice it can be difficult to produce a low-cost diagnostic device using such a complex series of steps, and to date manufacturing costs have limited deployment of these types of diagnostic devices to resource-limited settings such as developing nations. To provide enhanced diagnostic resources and improve health care these areas, there remains a need for multiplexed assay devices that are inexpensive, portable, and easy to construct and use.

SUMMARY

In general, the present disclosure is directed to inexpensive, easy to use diagnostic devices for quantitative or qualitative analysis of a sample fluid including an analyte. Suitable sample fluids include, but are not limited to, body fluids (e.g., blood, sputum, saliva, or urine), industrial fluids, water samples, and the like. The diagnostic device includes at least two portions, each portion made from a hydrophilic material such as paper. The planar portions are stacked on each other and each occupy a different and substantially parallel plane to form a three-dimensional structure. At least one of the planar portions includes a hydrophobic region and a hydrophilic region. The hydrophobic region in each substrate portion is formed by applying a low surface energy material, such as a hydrophobic ink, which extends through a thickness of the substrate portion from a first major surface to a second major surface thereof. The hydrophobic region in each substrate portion includes an arrangement of interconnected pores having at least one uninterrupted path that extends between the first major surface and the second major surface. The hydrophilic regions in the overlying substantially parallel substrate portions can be aligned with each other such that a fluid is passively transported between adjacent hydrophilic regions to provide a sample flow path between adjacent substrate portions that is substantially normal to the overlying planes of the substrate portions.

In some embodiments, some surfaces of the overlying substrate portions may optionally include connective regions that maintain the alignment of the hydrophobic and hydrophilic regions and the sample flow path. In some embodiments, the diagnostic device can include a mechanical fastener to maintain the alignment of the hydrophobic and hydrophilic regions.

In various embodiments, a reagent is within the sample flow path, in fluid communication with the sample flow path, or may be applied to the sample flow path, to provide an indication of at least one of a presence, absence, or concentration of an analyte in the sample. For example, in some embodiments, the indication includes an easily readable color change.

In one embodiment, the diagnostic device includes an elongate hydrophilic substrate with folded regions dividing the substrate into at least two portions, each portion occupying a different and substantially parallel plane. When the substrate is folded, the planar portions are stacked adjacent to each other to provide a diagnostic device with a three-dimensional structure.

The disclosed diagnostic devices are particularly well adapted to conduct immunoassays, such as sandwich or competitive immunoassays, although they may be readily adapted to execute assay formats including steps such as, for example, filtration, multiple incubations with different reagents or combinations of reagents, serial or timed addition of reagents, various incubation times, washing, and the like. The diagnostic devices are particularly effective for executing colorimetric assays, e.g., immunoassays with a color change as a readout, and are easily adapted to execute multiple assays simultaneously. They are extremely sensitive, simple to manufacture, inexpensive, and versatile.

In one aspect, the present disclosure is directed to a diagnostic device including an elongate substantially planar porous substrate with a first end and a second end, wherein the substrate has at least one folded region between the first end and the second end. A first portion of the substrate lies in a first plane with respect to the folded region, wherein the first portion of the substrate includes a first hydrophobic region and a first hydrophilic region, wherein the first hydrophobic region includes a first low surface energy polymeric material extending from a first major surface of the first portion of the substrate to a second major surface of the first portion of the substrate, and wherein the first hydrophobic region has an arrangement of interconnected open pores providing at least one uninterrupted path extending from the first major surface of the first portion of the substrate to the second major surface of the first portion of the substrate. A second portion of the substrate lies in a second plane with respect to the folded region, wherein the second plane is substantially parallel to the first plane, the second portion of the substrate including a second hydrophilic region and a second hydrophobic region having a second low surface energy polymeric material, which may be the same or different from the first low surface energy polymeric material, extending from a first major surface of the second portion of the substrate to second major surface of the second portion of the substrate, and wherein the second hydrophobic region has an arrangement of interconnected open pores providing at least one uninterrupted path extending from the first major surface of the second portion of the substrate to the second major surface of the second portion of the substrate. At least one connective region is between the first portion of the substrate and the second portion of the substrate, wherein the at least one connective region is configured to maintain alignment of the first hydrophilic region and the second hydrophilic region sufficient to provide a sample flow path between the first portion of the substrate and the second portion of the substrate along a direction normal to the first plane and the second plane. A reagent is along the sample flow path, wherein the reagent is selected to detect at least one of a presence, an absence or a concentration of an analyte present in a sample applied to the diagnostic device.

In another aspect, the present disclosure is directed to a diagnostic device that includes an elongate substantially planar porous fibrous substrate with a first end and a second end. The substrate includes a plurality of folded regions between the first end and the second end, the plurality of folded regions dividing the planar porous substrate into a stack of overlying substantially planar panels, wherein each of the panels in the stack occupies a different substantially parallel plane, and wherein each of the panels includes: a hydrophobic area with fibers coated with a hydrophobic low surface energy polymeric ink such that open areas remain between the fibers, the open areas between the fibers providing at least one uninterrupted open path between a first major surface of the panel and a second major surface of the panel, and a hydrophilic area. At least some of the panels includes a reagent selected to detect an analyte present in a sample, and a connective region configured to attach adjacent panels to each other; and wherein the hydrophobic areas and hydrophilic areas in adjacent panels of the stack are aligned with each other to provide a sample flow path between the hydrophilic areas thereof along a direction normal to the first plane and the second plane such that the sample contacts the reagent disposed in the flow path to provide an indication of at least one of the presence, absence or concentration of the analyte in the sample.

In another aspect, the present disclosure is directed to a diagnostic method, the method including: providing a diagnostic device including an elongate substantially planar porous fibrous substrate with a first end and a second end, wherein the substrate has a plurality of folded regions between the first end and the second end, the plurality of folded regions dividing the planar porous substrate into a stack of overlying planar panels each occupying a different substantially parallel plane, and wherein each of the panels includes: a hydrophobic area and a hydrophilic area arranged such that the hydrophilic areas in the panels are registered with each other to provide a sample flow path therebetween, the hydrophobic areas including fibers coated with a low surface energy polymeric material such that open areas remain between the fibers, the open areas between the fibers providing at least one uninterrupted open path between a first major surface of the panel and a second major surface of the panel; a reagent disposed in the sample flow path, and a connector between at least some of the panels that maintains the alignment of the hydrophilic regions along the sample flow path; applying a sample to the sample flow path; and flowing the sample by capillary action along the sample flow path such that the reagent provides an indication of at least one of a presence, absence, or a concentration of the analyte in the sample.

In another aspect, the present disclosure is directed to a method of making a diagnostic device, the method including: applying a hydrophobic hardenable polymeric ink composition to an elongate web of a fibrous material, wherein the hydrophobic hardenable polymeric ink composition is applied in a plurality of adjacent web regions extending from a first edge of the web to a second edge of the web, wherein each web region is separated from adjacent web regions by a border region; each and wherein each web region includes: a hydrophobic area including the hydrophobic polymeric ink composition, a hydrophilic area substantially free of the hydrophobic polymeric ink composition, and at least partially hardening the hardenable polymeric ink composition in the hydrophobic areas of each web region to provide a hydrophobic ink on fibers of the fibrous material and open areas between the fibers, the open areas between the fibers providing at least one uninterrupted open ink-free path between a first major surface of the web and a second major surface of the web; and folding the web of porous material along the border regions to form a stack of overlying substantially planar panels, wherein each of the overlying planar panels in the stack occupies a different substantially parallel plane, and wherein each of the overlying planar panels includes registered hydrophilic areas forming a sample flow path therebetween.

In another aspect, the present disclosure is directed to a system, including a diagnostic device with an elongate substantially planar porous substrate with a first end and a second end, wherein the substrate has at least one folded region between the first end and the second end, and wherein: a first portion of the substrate lies in a first plane with respect to the folded region, wherein the first portion of the substrate has a first hydrophobic region and a first hydrophilic region, wherein the first hydrophobic region includes a hydrophobic polymeric low surface energy material extending from a first major surface of the first portion of the substrate to a second major surface of the first portion of the substrate, and wherein the first hydrophobic region includes an arrangement of interconnected open pores providing at least one uninterrupted path extending from the first major surface of the first portion of the substrate to the second major surface of the first portion of the substrate; and a second portion of the substrate, different from the first portion of the substrate, wherein the second portion of the substrate lies in a second plane with respect to the folded region, wherein the second plane is substantially parallel to the first plane, the second portion of the substrate including a second hydrophilic region and a second hydrophobic region including the hydrophobic polymeric low surface energy material and extending from a first major surface of the second portion of the substrate to second major surface of the second portion of the substrate, and wherein the second hydrophobic region has an arrangement of interconnected open pores providing at least one uninterrupted path extending from the first major surface of the second portion of the substrate to the second major surface of the second portion of the substrate; at least one connective region between the first portion of the substrate and the second portion of the substrate, wherein the at least one connective region is configured to maintain alignment of the first hydrophilic region and the second hydrophilic region sufficient to provide a passive sample flow path between the first portion of the substrate and the second portion of the substrate along a direction normal to the first plane and the second plane; and a reagent selected to detect at least one of a presence, an absence or a concentration of an analyte present in a sample fluid applied to flow path of the diagnostic device.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 3B is a schematic cross-sectional view of the diagnostic device of FIG. 3A.

Like symbols in the drawings indicate like elements.

DETAILED DESCRIPTION

Figure 1A:
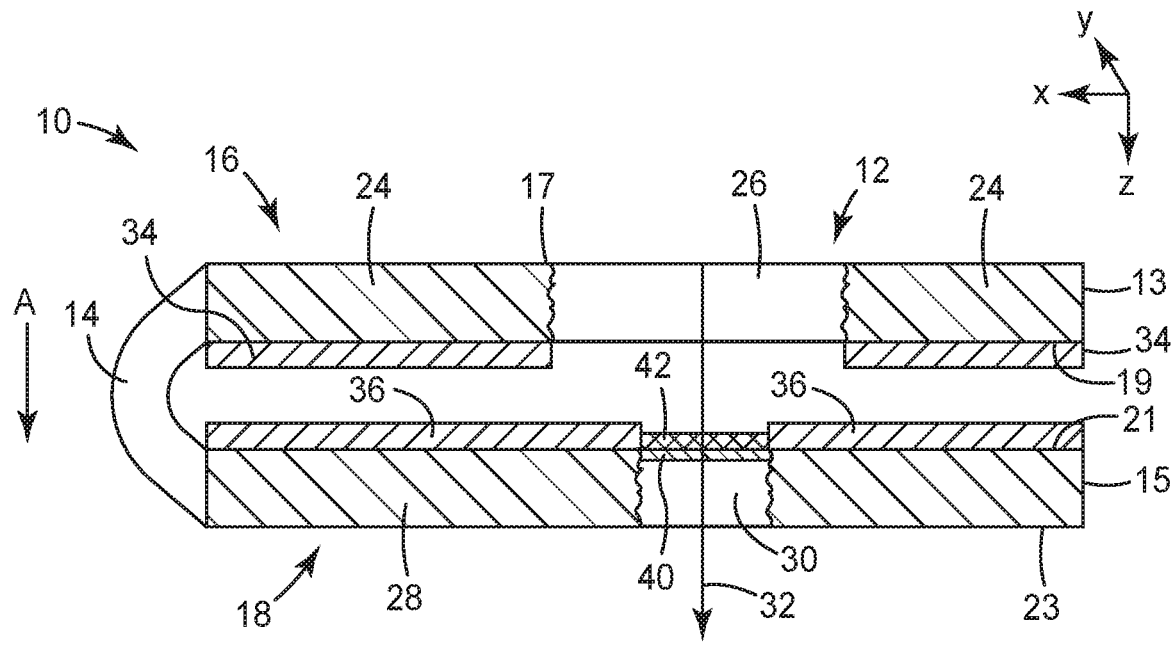
FIG. 1A is schematic cross-sectional view of an embodiment of a diagnostic device according to the present disclosure.
Figure 1B:
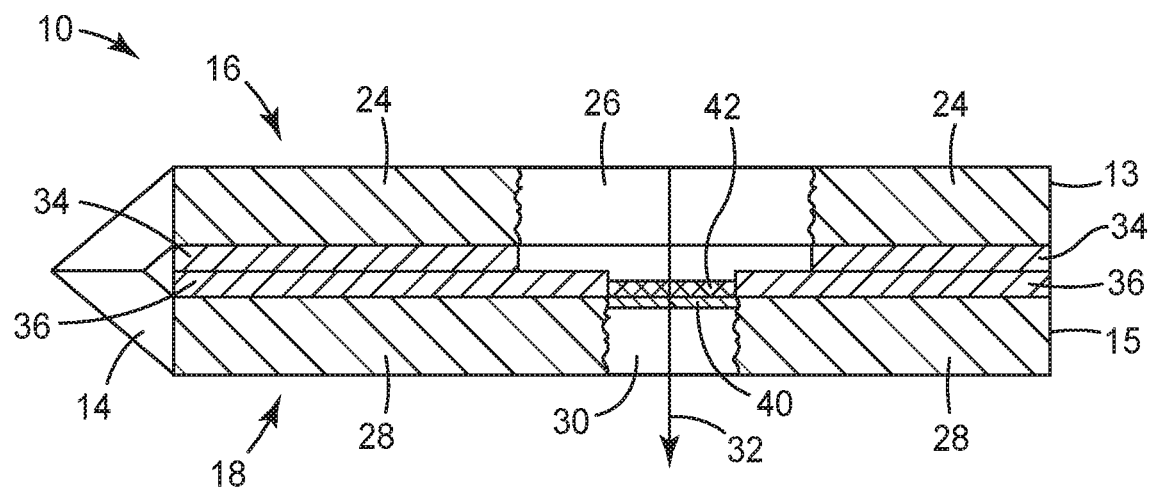
FIG. 1B is schematic cross-sectional view of an embodiment of a diagnostic device according to the present disclosure.

Referring now to FIGS. 1A-1B, an embodiment of a diagnostic device 10 includes an elongate substantially planar hydrophilic substrate 12 with a first end 13, a second end 15, and at least one folded region 14 between the first and the second ends 13, 15. The folded region 14 separates the hydrophilic substrate 12 into a first sheet-like portion 16 and a second sheet-like portion 18, each occupying a substantially parallel plane with respect to the folded region 14. The first substrate portion 16 includes a first major surface 17 and a second major surface 19, while the second substrate portion 18 includes a first major surface 21 and a second major surface 23. In the embodiment of FIG. 1A, the first portion of the substrate 16 and the second portion of the substrate 18 overlie one another such that the respective major surfaces 19 and 21 are adjacent to each other.

The first substrate portion 16 includes a first hydrophobic region 24 and a first hydrophilic region 26, while the second substrate portion 18 includes a second hydrophobic region 28 and a second hydrophilic region 30. The fibers of the substrate 12 in the hydrophobic regions 24, 28 have applied thereto a low surface energy polymeric material, and as such resist unassisted capillary fluid flow or wicking of a selected fluid, such as, for example, a sample fluid including, for example, an analyte, or a buffer or a wash solution, therethrough. As a result of this resistance, the selected fluid is passively transported (requiring no external pressure gradients, gravitational or electrostatic forces) between the hydrophilic regions 26, 30. The hydrophobic regions 24, 28 substantially confine the flow of the fluid along the direction of the arrow A, which is aligned along thickness of the substrate portions 16, 18, or along the z-axis of the three-dimensional diagnostic device 10. The hydrophilic regions 26, 30 are sufficiently aligned with each other such that a fluid sample placed on the first hydrophilic region 26 (not shown in FIGS. 1A-1B, see FIGS. 1C-1D) can be passively transported using, for example, wicking or capillary action, along a sample flow path 32 to provide fluid communication between the first substrate portion 16 and the second substrate portion 18 such that the fluid sample wicks into the second hydrophilic region 30.

Figure 1C:
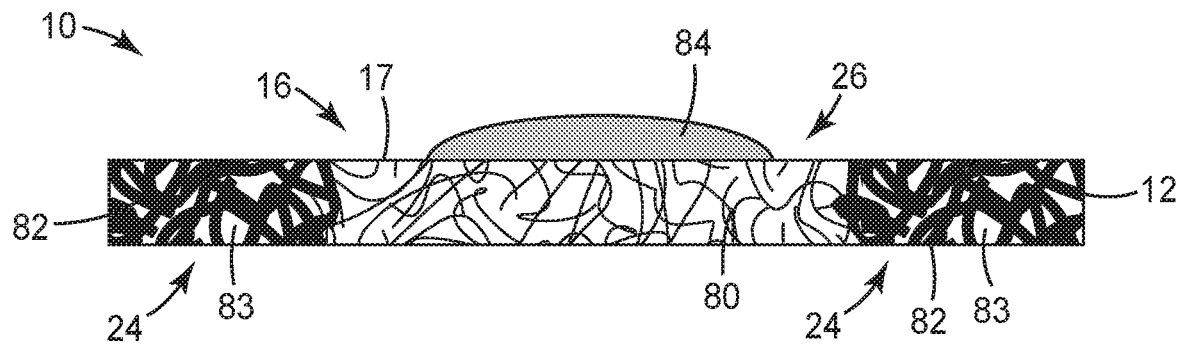
FIG. 1C is magnified schematic cross-sectional view of a portion of the embodiment of the diagnostic device of FIGS. 1A-1B when a fluid is initially applied.
Figure 1D:
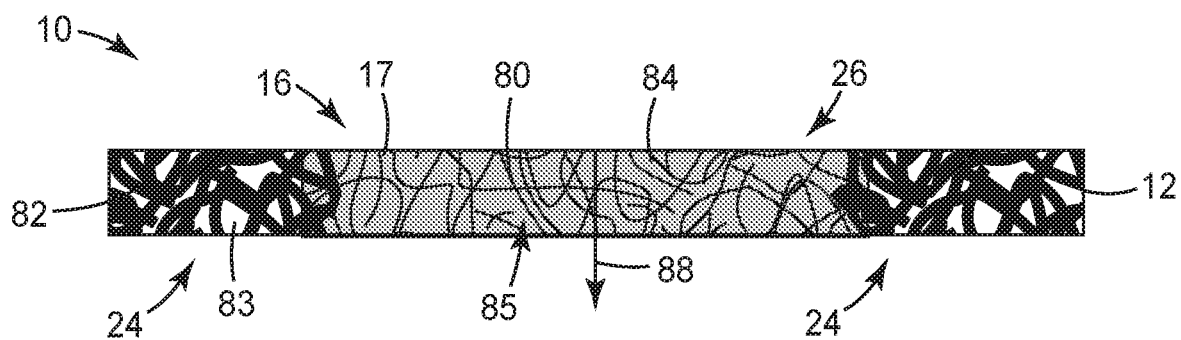
FIG. 1D is magnified schematic cross-sectional view of the embodiment of the diagnostic device of FIG. 1C after the fluid was passively transported into and wet a portion of the substrate thereof.

Referring now to the magnified schematic cross-sectional diagrams in FIGS. 1C-1D, the diagnostic device 10 of FIGS. 1A-1B includes a hydrophilic substrate 12 with a first substrate portion 16. The substrate portion 16 of the hydrophilic substrate 12 includes a hydrophobic portion 24 and a hydrophilic portion 26. The hydrophilic portion 26 includes an arrangement of entangled fibers 80. In some example embodiments, which are not intended to be limiting and are provided only as an illustrative example, the fibers 80 in the hydrophilic region 26 have a surface energy σ at a selected temperature for a selected liquid 84 of about 40 to about 65 dynes/cm. In the hydrophobic portion 24, at least a portion of the fibers 80 are coated with a low-surface energy polymeric material 82, which limits capillary flow (or wicking) of a fluid into the hydrophobic portion 24. In some embodiments, if the low surface energy polymeric material 82 is deposited on the fibers 80 such that it only coats the surface of the fibers, at least some interconnected interstitial passages 83 remain between the fibers. The passages 83 remain open such that a gas (which is a fluid) may freely move through the porous substrate 12 in the hydrophobic regions 24. After coating with the low surface energy polymeric material 82, the fibers in the hydrophobic regions 24 have a surface energy at least 10 dyne/cm less than the surface tension of the liquid 84.

If the liquid 84 is placed on the surface 17 of the hydrophilic region 26 at a time t=0, after a saturation time $t_{sat}$ greater than t=0 has elapsed, the fluid 84 will wick and be passively transported along the fibers 80 and occupy interstitial regions 85 in the hydrophilic region 26. The low surface energy polymeric material in the hydrophobic regions 24 tends to repel or resist intrusion of the fluid 84 into the interstitial regions 83 therein, thereby forming a flow path 88 through the hydrophilic region 26 for the fluid 84.

Referring again to FIGS. 1A-1B, all or a portion of one or both of the hydrophilic regions 26, 30 can include a test area 42 where an analytical result or output of the device 10 can be displayed for a user, as well as one or more reagents 40 in the test area 42 or in fluid communication with the test area 42. The reagents 40 are selected to provide an indication of at least one of a presence, absence or concentration of an analyte in the fluid sample are disposed in the sample flow path 32. In various embodiments, the reagent 40 is applied to all or a portion of one or both of the hydrophilic regions 26, 30, can be in another portion of the device 10 and in fluid communication with the flow path 32, or can be applied to the sample flow path 32 before or after the application of the fluid sample to the sample flow path 32.

In some embodiments, the diagnostic device 10 includes an optional first connection region 34 on the second major surface 19 of the first substrate portion 16. In some embodiments, the diagnostic device 10 further includes an optional second connection region 36 on the first major surface 21 of the second substrate portion 18. Either or both of the adjacent major surfaces 19, 21 of the overlying substrate portions 16, 18 can include connection regions, which adhere the first substrate portion 16 to the second substrate portion 18 and maintain the registration of the hydrophilic regions 26, 30 to preserve the sample flow path 32 (FIG. 1B).

In various embodiments, the elongate hydrophilic substrate 12 may be made from any porous, hydrophilic, adsorbent material capable of wicking a sample fluid by capillary action. In one or more embodiments, the substrate 12 is a paper product such as, for example, chromatographic paper, filter paper, and the like, but may also be chosen from woven or nonwoven fabrics, or from polymer films such as, for example, nitrocellulose, cellulose acetate, polyesters, and polyurethane, and the like.

The first and second hydrophobic regions 24, 28 may be formed by applying a desired pattern of a low surface energy polymeric material such as, for example, a polymeric ink composition, to the substrate 12. As shown schematically in FIGS. 1C-1D, the hydrophobic ink composition wicks along the fibers of the hydrophilic substrate 12 and coats the fibers thereof, leaving open at least some interstitial regions between the fibers. When subsequently cured or hardened, the polymeric ink composition provides open interstitial regions that form at least one uninterrupted open path between the respective major surfaces 17, 19 of the first substrate portion 16 and major surfaces 21, 23 of the second substrate portion 18. The hydrophobic regions 24, 28 thus resist absorption of a liquid applied to, for example, the hydrophilic region 26 of the first substrate portion 16, and the liquid is passively transported via capillary action or wicking between the hydrophilic regions 26, 30.

While not wishing to be bound by any theory, currently available evidence indicates that the relative difference in absorption between the hydrophobic regions 24, 28 and the hydrophilic regions 26, 30 is a function of difference between the surface energy of the fibers in the hydrophilic regions for a selected liquid such as, for example, a sample fluid, a buffer, and the like, which are intended to flow between the substrate portions 16, 18, and the surface energy of the fibers coated with the low surface energy ink in the hydrophobic regions 24, 28. The larger this difference, the larger the resistivity to absorption of the selected fluid in the hydrophobic regions 24, 28. The difference may also depend on, for example, the uniformity of ink coverage, the structure of the fibers, and the like.

In one example, if the sample fluid selected to flow by wicking or capillary action between the substrate portions 16, 18 is a bodily fluid, the surface energy of the fibers with the low surface energy hydrophobic ink applied thereto in the hydrophobic regions 24, 28 should be lower than the lowest value of the surface tension of the bodily fluid. Because bodily fluids have a range of surface tensions, the surface energy of the fibers in the hydrophobic regions 24, 28 should be at least 10 dyne/cm lower than the lowest surface tension of the bodily fluid, or at least 15 dyne/cm lower, or at least 20 dyne/cm lower, or even at least 30 dyne/cm lower. For example, it is reported that human urine has a minimum surface tension of about 55 dyne/cm, and human saliva has a surface tension of about 40 dyne/cm, so to resist absorption of these bodily fluids by wicking or capillary action the hydrophobic regions 24, 28 surface energy of ink should have a surface tension of less than about 45 dyne/cm, or less than about 40 dyne/cm, or less than about 35 dyne/cm, or less than about 30 dyne/cm, or less than about 25 dyne/cm, or less than about 20 dyne/cm.

In another example, to resist capillary flow or wicking of a selected fluid, presently available evidence indicates that the hydrophobic ink compositions in the regions 24, 28, when hardened, provide a contact angle for the selected fluid of greater than about 90°, or greater than about 95°, or greater than about 100°, or greater than about 105°, or greater than about 110°, or greater than about 115°, or greater than about 120°, or greater than about 125°, or greater than about 130°, or greater than about 135°, or even greater than about 140°.

Contact angles and wettability may be measured using the techniques described in, for example, CAPILLARITY AND WETTING PHENOMENA DROPS, BUBBLES, PEARLS, WAVES by Francoise Brochard-Wyart; David Quere, Hardcover; New York: Springer, Sep. 12, 2003; WETTABILITY (SURFACTANT SCIENCE) by John Berg, ed., CRC Press; 1 edition, Apr. 20, 1993, each of which are incorporated herein by reference in their entirety.

In various embodiments, the hydrophobic ink composition includes at least one polymerizable low surface energy monomer, oligomer, or polymer that can provide a desired resistance to absorption of a selected liquid or sample fluid. This low surface energy monomer, oligomer, or polymer can be a fluorocarbon, silicone, or hydrocarbon. The low surface energy monomer, oligomer, or polymer is added to the formulation to reduce the surface energy of the cured hydrophobic coating to a wetting tension of from about 30 to less than about 38 mJ/m2 as measured by ASTM D 2578-08. Examples of suitable polymerizable low surface energy monomers, oligomers and polymers are described in WO2011/094342, which is incorporated by reference herein in its entirety.

In some embodiments, the hydrophobic region 24, 28 includes a non-tacky crosslinked polymeric layer. This polymeric layer is made from a radiation curable coating formulation containing at least one low surface energy monomer, oligomer, or polymer chosen from the group of polymerizable fluorocarbon, silicone, or hydrocarbon monomers.

The non-tacky crosslinked polymeric layer may be formed by polymerizing a precursor composition, although other methods (e.g., crosslinking of a polymer or blend thereof using chemical means or ionizing radiation) may also be used. Useful precursor compositions typically include one or more polymerizable materials (e.g., monomers and/or oligomers, which may be monofunctional and/ or polyfunctional), a curative, and optionally inorganic particles. Polymerizable materials may be, for example, free-radically polymerizable, cationically polymerizable, and/or condensation polymerizable.

Useful polymerizable materials include, for example, acrylates and methacrylates, epoxies, polyisocyanates, and trialkoxysilane terminated oligomers and polymers. Preferably, the polymerizable material includes a free-radically polymerizable material.

Useful free-radically polymerizable materials include, for example, free-radically polymerizable monomers and/or oligomers, either or both of which may be monofunctional or multifunctional. Exemplary free-radically polymerizable monomers include styrene and substituted styrenes (e.g., a-methylstyrene); vinyl esters (e.g., vinyl acetate); vinyl ethers (e.g., butyl vinyl ether); N-vinyl compounds (e.g., N-vinyl-2- pyrrolidone, N-vinylcaprolactam); acrylamide and substituted acrylamides (e.g., N,N- dialkylacrylamides); and acrylates and/or methacrylates (i.e., collectively referred to herein as (meth)acrylates) (e.g., isooctyl (meth) acrylate, nonylphenol ethoxylate (meth)acrylate, isononyl (meth)acrylate, diethylene glycol (meth)acrylate, isobornyl (meth)acrylate, 2-(2-ethoxyethoxy)ethyl (meth)acrylate, 2-ethylhexyl (meth)acrylate, lauryl (meth)acrylate, butanediol mono(meth)acrylate, (β-carboxyethyl (meth)acrylate, isobutyl (meth)acrylate, 2-hydroxyethyl (meth)acrylate, (meth)acrylonitrile, isodecyl (meth)acrylate, dodecyl (meth)acrylate, n-butyl(meth)acrylate, methyl (meth)acrylate, hexyl (meth)acrylate, (meth)acrylic acid, stearyl (meth)acrylate, hydroxy functional polycaprolactone ester (meth)acrylate, hydroxyethyl (meth)acrylate, hydroxymethyl (meth)acrylate, hydroxypropyl (meth)acrylate, hydroxyisopropyl (meth)acrylate, hydroxybutyl (meth)acrylate, hydroxyisobutyl (meth)acrylate, tetrahydrofurfuryl (meth)acrylate, ethylene glycol di(meth)acrylate, hexanediol di(meth)acrylate, triethylene glycol di(meth)acrylate, 1,3-propylene glycol di(meth)acrylate, tetraethylene glycol di(meth)acrylate, trimethylolpropane tri(meth)acrylate, 1,4-cyclohexanediol di(meth)acrylate, 1,5- pentanediol di(meth) acrylate, ethoxylated trimethylolpropane tri(meth)acrylate, glycerol tri(meth)acrylate, pentaerythritol tri(meth)acrylate, pentaerythritol tetra(meth)acrylate, dipentaerythritol penta(meth)acrylate, and neopentyl glycol di(meth)acrylate).

Exemplary free-radically polymerizable oligomers include those marketed by UCB Chemicals, Smyrna, Georgia (e.g., under the trade designation "EBECRYL"), and those marketed by Sartomer Company, Exton, PA (e.g., under the trade designations "KAYARAD" or "CN").

Depending on the choice of polymerizable material, the precursor composition may, optionally, contain one or more curatives that assist in polymerizing the polymerizable material. The choice of curative for specific polymerizable materials depends on the chemical nature of the copolymerizable material. For example, in the case of epoxy resins, one would typically select a curative known for use with epoxy resins (e.g., dicyandiamide, onium salt, or polymer-captan). In the case of free-radically polymerizable resins, free radical thermal initiators and/or photoinitiators are useful curatives.

Typically, the optional curative(s) is used in an amount effective to facilitate polymerization of the monomers and the amount will vary depending upon, for example, the type of curative, the molecular weight of the curative, and the polymerization process. The optional curative(s) is typically included in the precursor composition in an amount in a range of from about 0.01 percent by weight to about 10 percent by weight, based on the total weight of the precursor composition, although higher and lower amounts may also be used. The precursor composition may be cured, for example, by exposure to a thermal source (e.g., heat, infrared radiation), electromagnetic radiation (e.g., ultraviolet and/ or visible radiation), and/or particulate radiation (e.g., electron beam of gamma radiation).

A variety of curing strategies can be readily selected, determined in part upon the characteristics of the curable coating composition, other components of the article, as well as manufacturing facilities. Illustrative techniques for maximizing the cure of a UV cured coating composition include curing under nitrogen, using new UV bulbs, cleaning the UV bulbs before use, matching the output spectrum of the UV bulb to the absorption of the initiator, and treatment at a slow speed and/or for a longer time. In some embodiments, a certain amount of post-exposure cure may take place over time as the dry erase article ages at room temperature.

A second cure treatment may be required in addition to the first cure described above. The second cure may use the same radiation source as the first cure, or it may use a different radiation source. Preferred second cure methods include heat, electron beam, and gamma ray treatment.

If the optional curative is a free-radical initiator, the amount of curative is preferably in a range of from about 1 percent by weight to about 5 percent by weight, based on the total weight of the precursor composition, although higher and lower amounts may also be used. Useful free-radical photoinitiators include, for example, benzoin ethers such as benzoin methyl ether and benzoin isopropyl ether, substituted benzoin ethers (e.g., anisoin methyl ether), substituted acetophenones (e.g., 2,2- dimethoxy-2-phenylacetophenone), substituted alpha-ketols (e.g., 2-methyl-2-hydroxypropiophenone), benzophenone derivatives (e.g., benzophenone), and acylphosphine oxides. Exemplary commercially available photoinitiators include photoinitiators under the trade designation "IRGACURE" (e.g., IRGACURE 651, IRGACURE 184, and IRGACURE 819) or "DAROCUR" (e.g., DAROCUR 1173, DAROCUR 4265) from Ciba Specialty Chemicals, Tarrytown, New York, and under the trade designation "LUCIRIN" (e.g., "LUCIRIN TPO") from BASF, Parsippany, New Jersey.

Exemplary free-radical thermal initiators include peroxides such as benzoyl peroxide, dibenzoyl peroxide, dilauryl peroxide, cyclohexane peroxide, methyl ethyl ketone peroxide, hydroperoxides, for example, tert- butyl hydroperoxide and cumene hydroperoxide, dicylohexyl peroxydicarbonate, t-butyl perbenzoate, and azo compounds, for example, 2, 2,-azo-bis(isobutyronitrile).

The low surface energy monomers, oligomers, or polymers may be chosen from the group of fluorocarbon, silicone, or hydrocarbon monomers. Fluorocarbon monomers suitable for the hydrophobic ink composition include but are not limited to perfluoro acrylates or methacrylates, e.g., C4F9 based sulfonamide acrylates and C3F7 based sulfonamide acrylates.

Fluorochemical oligomers suitable for use in the hydrophobic ink compositions herein include the commercially available chemicals FLUORAD™ FC-4430 and FC-4432 from 3M Company, St. Paul, MN. Suitable fluorochemical polymers include perfluoropolyether polymers with poly(alkylene oxide) repeat units, e.g., as described in PCT Application No. WO2009/076389 (Yang et al). Suitable silicone monomers include, but are not limited to, silicone acrylate monomers. Exemplary silicone acrylate monomers suitable for use herein include BYK-371 Reactive Silicone Surface Additive, BYK-373 Reactive Silicone Surface Additive. BYK-377 Reactive Silicone Surface Additive, BYK-UV 3500 Surface Additives for Radiation Curable Systems, BYK-UV 3530 Surface Additives for Radiation Curable Systems, BYK-UV 3570 Surface Additives for Radiation Curable Systems, and BYK SILCLEAN 3710 Surface Additives to Improve Surface Cleanability from BYK- Chemie GmBH, Wesel, Germany. Other suitable silicone monomers include TEGORAD™ 2100, TEGORAD™ 2200N, TEGORAD 2250, and TEGORAD 2300 silicone acrylate monomers from Evonik Goldschmidt Corporation. Hopewell, VA.

Hydrocarbon monomers can be used to reduce the surface energy of a coating. Those hydrocarbon monomers are characterized by a long side chain that can form a crystalline structure on a surface. Suitable hydrocarbon monomers include but are not limited to octadecyl acrylate.

In one embodiment, the low surface energy monomers, oligomers, or polymers are added to a coating formulation in a concentration sufficient to produce a cured coating with a wetting tension of from about 20 to about 40 mJ/m$^2$. In some embodiments, the wetting tension of the cured coating is from about 30 to about 36 mJ/m$^2$.

In some embodiments, the radiation curable material includes the foregoing oligomer(s), monomer(s) and/or polymer(s) in one or more solvents along with a volume of optional particles or nanoparticles, eg., to impart increased hardness and durability to the writing member. In some cases, dilution of the hydrophobic ink in solvent can promote faster wicking into the porous or fibrous substrate (by lowering the viscosity of the ink) and can leave more interconnected space between the fibers.

Nanoparticles can be surface modified which refers to the fact that the nanoparticles have a modified surface so that the nanoparticles provide a stable dispersion. "Stable dispersion" refers to a dispersion in which the colloidal nanoparticles do not agglomerate after standing for a period of time, such as about 24 hours, under ambient conditions, e.g., room temperature (i.e., about 20 to about 22° C.), and atmospheric pressure, without extreme electromagnetic forces.

Surface-modified colloidal nanoparticles can optionally be present in a polymer coating used as a coatable composition herein with nanoparticles present in an amount effective to enhance the durability of the finished or optical element. The surface- modified colloidal nanoparticles described herein can have a variety of desirable attributes, including, for example, nanoparticle compatibility with a coatable composition such that the nanoparticles form stable dispersions within the coatable composition, reactivity of the nanoparticle with the coatable composition making the composite more durable, and a low impact or uncured composition viscosity. A combination of surface modifications can be used to manipulate the uncured and cured properties of the composition. Surface-modified nanoparticles can improve optical and physical properties of the coatable composition such as, for example, improved resin mechanical strength, minimized viscosity changes while increasing solids volume loading in the coatable composition and maintain optical clarity while increasing solid volume loading in the coatable composition.

In some embodiments, the nanoparticles are surface-modified nanoparticles. Suitable surface-modified colloidal nanoparticles can comprise oxide particles. Nanoparticles may comprise a range of particle sizes over a known particle size distribution for a given material In some embodiments, the average particle size may be within a range from about 1 nm to about 100 nm. Particle sizes and particle size distributions may be determined in a known manner including, for example, by transmission electron microscopy ("TEM"). Suitable nanoparticles can comprise any of a variety of materials such as metal oxides selected from alumina, tin oxide, antimony oxide, silica, zirconia, titania and combinations of two or more of the foregoing. Surface-modified colloidal nanoparticles can be substantially fully condensed.

In some embodiments, silica nanoparticles can have a particle size ranging from about 5 to about 100 nm. In some embodiments, silica nanoparticles can have a particle size ranging from about 10 to about 30 nm. Silica nanoparticles can be present in the coatable composition in an amount from about 10 to about 100 phr. In some embodiments, silica nanoparticles can be present in the coatable composition in an amount from about 30 to about 90 phr. Silica nanoparticles suitable for use in the coatable compositions of the present disclosure are commercially available from Nalco Chemical Co. (Naperville, IL) under the product designation NALCO COLLOIDAL SILICAS. Suitable silica products include NALCO products 1040, 1042. 1050, 1060, 2327 and 2329. Suitable turned silica products include, for example, products sold under the AEROSIL series OX-50, -130, -150, and -200 available from DeGussa AG. (Hanau, Germany), and CAB-O-SPERSE 2095, CAB-O-SPERSE A 105, and CAB-O-SIL MS available from Cabot Corp. (Tuscola, IL). Surface-treating the nanosized particles can provide a stable dispersion in the coatable composition (e.g.. a polymeric resin). Preferably, the surface- treatment stabilizes the nanoparticles so that the particles will be well dispersed in the coatable composition and results in a substantially homogeneous composition.

Furthermore, the nanoparticles can be modified over at least a portion of its surface with a surface treatment agent so that the stabilized particle can copolymerize or react with the coatable composition during curing Silica nanoparticles can be treated with a surface treatment agent. Surface treatment agents suitable for particles to be included in the coatable composition include compounds such as, for example, isooctyl trimethoxy-silane, N-(3-triethoxysilylpropyl) methoxyethoxyethoxy ethyl carbamate (PEG3TES), SILQUEST A1230, N-(3-triethoxysilylpropyl) methoxy ethoxyethoxyethyl carbamate (PEG2TES), 3-(methacryloyloxy)propyl trimethoxysilane. 3 -acryloxypropyltrimethoxysilane, 3 -(methacryloyloxy)propyltriethoxysilane, 3-(methacryloxy)propylmethyldimelhoxysilane,3-(acryloyloxypropyl) methyldimethoxy silane. 3-(methacryloloxy)propyldimethylethoxysilane, 3-(methacryloyloxy)propyldimethy ethoxysilane, vinyldimethylethoxy silane, phenyltrimethoxysilane, n-octyltrimethoxysilane, dodecyltrimethoxysilane, octadecyltrimethoxysilane, propyltrimethoxysilane,hexyltrimethoxy silane, vinylmethyldiacetoxysilane, vinylmethyldiethoxysilane, vinyltriacetoxysilane, vinyltriethoxy silane. vinyltriisopropoxysilane,vinyltrimethoxy silane, vinyltriphenoxysilane, vinyltri-t-butoxysilane, vinyltrisisobutoxysilane, vinyltriisopropenoxysilane, vinyltris(2-methoxyethoxy)silane, styrylethyltrimethoxysilane, mercaptopropyltrimethoxysilane.3-glycidoxypropyltrimethoxysilane, acrylic acid, methacrylic acid. oleic acid, stearic acid, dodecanoic acid, 2-[2-(2-methoxyethoxy)ethoxy]acetic acid (MEEAA), beta-carboxyethylacrylate, 2-(2-methoxyethoxy)acetic acid, methoxyphenyl acetic acid, and mixtures of two or more of the foregoing.

In some embodiments, the average particle sizes (e.g., particle diameter) may be within the range from about 1 nm to about 1000 nm. In addition to the foregoing particle sizes, use of smaller and larger average particle sizes are also contemplated. In embodiments of the disclosure, at least a portion of the foregoing particles may be surface modified in the manner described above. In outer embodiments, all the particles are surface modified. In still other embodiments, none of the particles are surface modified.

As will be understood, coating compositions used to make the hydrophobic regions of the present disclosure may include optional additives to enhance or control characteristics as desired, e.g., rheology modifiers such as JAYLINK Rheology Modifiers, colorants (e.g., dyes and/or pigments). fire retardants, antioxidants, stabilizers, antiozonants, plasticizers, UV absorbers, hindered amine light stabilizers (HALS), etc The hydrophobic ink compositions suitable to form the hydrophobic regions 24, 28 may include any commercially available ink that creates a desired resistance to capillary flow or wicking of a selected liquid such as, for example, a sample fluid. Suitable examples include, but are not limited to, NAZDAR 9400 Series UV Flexo Inks or OP Series Inks (available from NAZDAR Ink Technologies of Shawnee, KS, United States) such as 9418 or OP 1028. In some embodiments, the ink composition is hardenable or curable with radiation, such as, for example ultraviolet (UV) light.

In some embodiments, the hydrophobic ink composition may include a solvent selected to provide, for example, optimal wicking properties along the fibers of the substrate 12. Suitable solvents include, but are not limited to, water, alcohols, ethers, ketones, esters, and mixtures and combinations thereof.

The hydrophobic regions 24, 28 may be patterned with the hardenable hydrophobic ink by any suitable technique including, but not limited to coating, screening, stamping, printing, photolithography, and combinations thereof. In some embodiments, the patterning technique may include heating the ink composition to a suitable temperature such that the ink wicks and flows along the fibers of the substrate, but does not occupy interstitial regions between the fibers. The interstitial regions in the hydrophobic regions 24, 28 are sufficiently open and interconnected to allow some fluid flow between the major surfaces 17, 19 and 21, 23 of the substrate 12, but a fluid flow rate between the major surfaces of the substrate 12 in the hydrophobic regions 24, 28 is significantly lower that that of the hydrophilic regions 26, 30, so that a fluid placed in the hydrophilic regions 26, 30 avoids the hydrophobic regions 24, 28 and remains in the hydrophilic regions 26, 30 to proceed along the sample flow path 32.

In various embodiments, the optional connection regions 34, 36 may vary widely, and can include any type of adhesive such as, for example, pressure sensitive adhesives, hot-melt adhesives, cohesive adhesives, and mixtures and combinations thereof. In the present application, the term cohesive adhesive refers to adhesive materials that adhere to each other, but have low adhesion, or no adhesion, to other non-adhesive surfaces.

Suitable pressure-sensitive adhesives ("PSAs") are defined herein as adhesives which exhibit permanent tack at room temperature. This property allows pressure-sensitive adhesives to adhere tenaciously upon application with only light finger pressure. PSAs have a balance of properties: adhesion, cohesion, stretchiness, and elasticity. Adhesion refers both to immediate adhesion to a surface and to the bond strength which develops upon application of pressure (often measured as "peel strength"). Cohesion refers to the "shear strength" or resistance of the applied PSA to failure when subjected to shearing forces. Stretchiness refers to the ability to elongate under low stresses. Elasticity refers to a property wherein the material exhibits a retractive force when stretched and retracts when the force is released. A general description of pressure-sensitive adhesives may be found in the Encyclopedia of Polymer Sciences and Engineering, Vol. 13, Wiley-Interscience Publishers (New York, 1988).

In one example embodiment, a suitable cohesive adhesive as utilized herein includes quick-drying adhesives that, once dried, will create a surface with essentially no tack and will only adhere to other surfaces coated with the same adhesive when placed under pressure. Cohesive adhesives bond to themselves at ambient temperature with pressure, yet are essentially tack free to the touch, allowing coated substrates to be folded or wound upon themselves and stored without adhering to the opposing face of the substrate backing.

In various embodiments, suitable cohesive adhesives include latex or water-based adhesive compositions that, after drying, are substantially tack free to the touch, yet will adhere to themselves at ambient temperature with a pressure of 100 psi, and preferably at a pressure of about 60 psi or less. The bond strength of the self-seal may vary depending on the coat weight, pressure, and dwell time used. However, at minimum the removal force is at least about 10 g/linear inch, typically at least about 20 g/linear inch, preferably at least 50 g/linear inch, and most preferably at least about 100 g/linear inch. Substantially tack free to the touch means that the dried composition is nonblocking.

The cohesive adhesive is further capable of being applied to a hydrophilic substrate material at a relatively high rate of production and of being dried relatively quickly. As a result, the cohesive adhesive enables the manufacture of relatively low-cost diagnostic devices at production rates much faster than conventional adhesive materials used in the art.

Adhesives of this type have been employed in a variety of packaging applications including food (i.e. flexible packaging for candy wrappers, chips etc.); medical packaging; self-seal and tamper evident envelopes; banding for paper money, napkins, and clothing; and protective packaging such as fold over "blister" packages for hardware and small parts.

In some embodiments, for example, the cohesive adhesive may be applied using a highspeed printing process to reduce film thickness, further enabling the manufacture of a diagnostic device at production rates much faster than conventional adhesive materials used in the art. In some embodiments, which are provided as examples and not intended to be limiting, suitable cohesive adhesives include emulsions of natural and/or synthetic latex rubber in aqueous solution of ammoniated water with a solids content between 15 and 65 percent by weight.

In some example embodiments, which are not intended to be limiting, the viscosity of a suitable cohesive adhesive may be between 10 and 450 centipoise (cP) at 20 revolutions per minute and 23° C. per ASTM D1084 Test Method B. In some embodiments, the density of cohesive adhesive may be between 8.0 and 9.0 pounds per gallon (lb/gal) at 25° C., and the basicity or pH may be between 9.5 and 12.

In various embodiments, the cohesive adhesive may optionally contain dispersants, surfactants, tackifiers, isocyanates, antioxidants, and antifoaming agents, as is well known in the art, without deviating from the scope of the disclosure.

In at least one embodiment of the present disclosure, which is not intended to be limiting, the cohesive adhesive has the following properties: the solids content is 57.5 percent by weight, the viscosity is 75 cP at 25° C., the density is 8.3 lb/gal, and the pH is 10.0. In at least one embodiment of the present disclosure, the adhesive has a solids content between 45 and 58 percent by weight, a viscosity between 75 and 200 cP at 23° C., a density between 8.3 and 8.7 lb/gal at °C, and a pH of 10 to 11.

In some embodiments, mechanical fasteners may be utilized to maintain the alignment of one or more of the hydrophilic regions in overlying layers or panels of the diagnostic device, either alone or in combination with any of the adhesive layers described above. Suitable mechanical fasteners include, but are not limited to, plastic or metal clips, staples, elastic bands such as plastic or rubber bands, plastic zip ties and combinations thereof.

In general, a wide variety of reagents 40 may be disposed in, or in fluid communication with, the test area 42 in hydrophilic regions 26, 30 of the diagnostic device 10 to detect one or more analytes in a sample fluid. These reagents include, but are not limited to, antibodies, nucleic acids, aptamers, molecularly-imprinted polymers, chemical receptors, proteins, peptides, inorganic compounds, and organic small molecules. In a given device, one or more reagents may be adsorbed to one or more hydrophilic regions 26, 30 (non-covalently through non-specific interactions), or covalently (as esters, amides, imines, ethers, or through carbon-carbon, carbon-nitrogen, carbon-oxygen, or oxygen-nitrogen bonds).

Any reagent 40 needed in the assay may be provided within, or in a separate adsorbent layer in fluid communication with the test area 42 within the hydrophilic regions 26, 30 and the sample flow path 32. Exemplary assay reagents include protein assay reagents, immunoassay reagents (e.g., ELISA reagents), glucose assay reagents, sodium acetoacetate assay reagents, sodium nitrite assay reagents, or a combination thereof. In various embodiments, which are not intended to be limiting, the diagnostic device 10 may include, a blocking agent, enzyme substrate, specific binding reagent such as an antibody or sFv reagent, labeled binding agent, e.g., labeled antibody, may be disposed in the device within or in flow communication with one or more of the hydrophilic regions 26, 30, or in a specific area thereof configured as a test area 42.

In some embodiments, a binder, e.g., an antibody, may be labeled with an enzyme or a colored particle to permit colorimetric assessment of analyte presence or concentration in a sample fluid. For example, the binder may be labeled with gold colloidal particles or the like as the color forming labeling substance. Where an enzyme is involved as a label, e.g., alkaline phosphatase, horseradish peroxidase, luciferase, or β-galactosidase, an enzyme substrate may be disposed in the device within or in flow communication with one of the hydrophilic regions 26, 30. Exemplary substrates for these enzymes include BCIP/NBT, 3,3′,5,5′-Tetramethylbenzidine (TMB), 3,3′-Diaminobenzidine (DAB), and 2,2′-azino-bis(3-ethylbenzthiazoline-6-sulphonic acid) (ABTS), 4-methylumbelliferphosphoric acid, 3-(4-hydroxyphenyl)-propionic acid, or 4-methylumbellifer-β-D-galactoside, or the like. In various embodiments, the reagent(s) 40 develop color in one or more test areas 42 along the sample path 32 (including gradations from white to black) as an indication of the presence, absence or concentration of an analyte in a sample.

In some embodiments, a device may include many reagents 40 disposed along the sample flow path, each of which can react with a different analyte to produce a detectable effect. Alternatively, the reagents 40 may be sensitive to a predetermined concentration of a single analyte.

In some embodiments, the reagent 40 may include a washing reagent, or plural wash reagents such as buffers or surfactant solutions, within or in fluid communication with a hydrophilic region 26, 30 or the sample flow path 32. Washing reagent(s) function to wash an analyte by removing unbound species within the hydrophilic regions 26, 30. For example, a suitable washing buffer may comprise PBS, detergent, surfactants, water, and salt. The composition of the washing reagent will vary in accordance with the requirements of the specific assay such as, for example, the particular capture reagent and indicator reagent employed to determine the presence of a target analyte in a test sample, as well as the nature of the analyte itself.

Alternatively, steps of a reaction using the devices disclosed herein may be washed as follows. In certain embodiments, defined hydrophilic regions 26, 30 do not contain a reagent 40. In such case, water or buffer is then added to the hydrophilic regions 26, 30 of the device 10 and the fluid passes through the device along the sample flow path 32 to provide a washing step for the analytes in the fluid sample. Such washing steps can be used to remove unbound analyte or other components added for the detection of the presence of an analyte.

The hydrophilic regions 26, 30 can include one or more test areas 42 that can be used to perform one or more assays for the detection of multiple analytes in the sample fluid. One or more of the hydrophilic regions 26, 30 can be treated with reagents 40 that respond to the presence of analytes in a sample fluid and provide an indicator of the presence of an analyte in the sample fluid. In some embodiments, the detection of an analyte in the sample fluid is visible to the naked eye and can provide a color indicator of the presence of the analyte. In various embodiments, indicators may include molecules that become colored in the presence of the analyte, change color in the presence of the analyte, or emit fluorescence, phosphorescence, or luminescence in the presence of the analyte. In other embodiments, radiological, magnetic, optical, and/or electrical measurements can be used to determine the presence of proteins, antibodies, or other analytes in the sample flow path 32.

In certain embodiments, analytes may be detected by direct or indirect detection methods that apply the principles of immunoassays (e.g., a sandwich or competitive immunoassay or ELISA).

In some embodiments, to detect a specific protein, one or more areas of the hydrophilic regions 26, 30 can be derivatized with reagents 40, such as antibodies, ligands, receptors, or small molecules that selectively bind to or interact with a protein in the sample fluid. For example, to detect a specific antigen in a sample, a test area 42 of the hydrophilic regions 26, 30 can be derivatized with reagents such as antibodies that selectively bind to or interact with that antigen. Alternatively, to detect the presence of a specific antibody in the sample fluid, a test area 42 of the hydrophilic regions 26, 30 may be derivatized with antigens that bind or interact with that antibody. For example, reagents 40 such as small molecules and/or proteins can be covalently linked to the hydrophilic regions 26, 30 using similar chemistry to that used to immobilize molecules on beads or glass slides, or using chemistry used for linking molecules to carbohydrates. In alternative embodiments, the reagents 40 may be applied and/or immobilized in the hydrophilic regions 26, 30 by applying a solution containing the reagent and allowing the solvent to evaporate (e.g., depositing reagent into the hydrophilic region). The reagents can be immobilized by physical absorption onto the porous substrate by other non-covalent interactions.

The interaction of certain analytes with some reagents may not result in a visible color change, unless the analyte was previously labeled. The devices disclosed herein may be additionally treated to add a stain or a labeled protein, antibody, nucleic acid, or other reagent that binds to the target analyte after it binds to the reagent 40 disposed in the sample flow path 32, which produces a visible color change. For example, the device 10 may include a separate area that already contains the stain, or labeled reagent, and includes a mechanism by which the stain or labeled reagent can be easily introduced into the sample flow path to bond to the target analyte after it binds to the reagent 40. Or, for example, the device 10 can be provided with a separate channel that can be used to flow the stain or labeled reagent from a different area of the hydrophilic regions 26, 30 into test area 42 along the sample flow path 32 to the target analyte after it binds to the reagent in the sample flow path. In one embodiment, this flow is initiated with a drop of water, or some other fluid. In another embodiment, the reagent and labeled reagent are applied at the same location in the device, for example, in a test area 42 of one of the hydrophilic regions 26, 30 along the sample flow path 32.

In one exemplary embodiment, ELISA may be used to detect and analyze a wide range of analytes and disease markers with the high specificity, and the result of ELISA can be quantified colorimetrically with the proper selection of enzyme and substrate.

Detection of an analyte in a sample fluid may include an additional step of creating digital data indicative of an image of a developed test area 42 and the assay result, and transmitting the data remotely for further analysis to obtain diagnostic information, or to store assay results in an appropriate database. Some embodiments further include equipment that can be used to image the device after deposition of the liquid to obtain information about the quantity of analyte(s) based on the intensity of a colorimetric response of the device. In some embodiments, the equipment establishes a communication link with off-site personnel, e.g., via cell phone communication channels, who perform the analysis based on images obtained by the equipment.

In some example embodiments, which are not intended to be limiting, the entire assay can be completed in less than 30 minutes, 20 minutes, 15 minutes, 10 minutes, or 5 minutes. In some example embodiments, the device 10 can have a detection limit of about 500 pM, 250 pm, 100 pM, 1 pM, 500 fM, 250 fM, or 100 fM.

The diagnostic device 10 of the present disclosure can be used for assaying small volumes of fluid samples. In various embodiments, the fluid samples that can be assayed include, but are not limited to, biological samples such as urine, whole blood, blood plasma, blood serum, sputum, cerebrospinal fluid, ascites, tears, sweat, saliva, excrement, gingival cervicular fluid, or tissue extract. In some embodiments, the volume of fluid sample to be assayed may be a drop of blood, e.g., from a finger prick, or a small sample of urine, e.g., from a newborn or a small animal. In some embodiments, the sample fluid is an environmental sample such as a water sample obtained from a river, lake, ocean or the like, or a sample of an industrial fluid. The device 10 may also be adapted for assaying non-aqueous fluid samples for detecting environmental contamination.

In some embodiments, a single drop of liquid, e.g., a drop of blood from a pinpricked finger, is sufficient to perform assays providing a simple yes/no answer to determine the presence of an analyte in a sample fluid, or a semi-quantitative measurement of the amount of analyte that is present in the sample, e.g., by performing a visual or digital comparison of the intensity of the assay to a calibrated color chart. However, to obtain a quantitative measurement of an analyte in the liquid, a defined volume of fluid is typically deposited in the device. Thus, in some embodiments, a defined volume of fluid (or a volume that is sufficiently close to the defined volume to provide a reasonably accurate readout) can be obtained by patterning the hydrophilic substrate 12 to include a sample well that accepts a defined volume of fluid. For example, in the case of a whole blood sample, the subject's finger could be pinpricked, and then pressed against the sample well until the well was full, thus providing a satisfactory approximation of the defined volume.

The assay reagents included in the device 10 are selected to provide a visible indication of the presence of one or more analytes in the sample fluid. The source or nature of the analytes that may be detected using the disclosed devices are not intended to be limiting. Exemplary analytes include, but are not limited to, toxins, organic compounds, proteins, peptides, microorganisms, bacteria, viruses, amino acids, nucleic acids, carbohydrates, hormones, steroids, vitamins, drugs, pollutants, pesticides, and metabolites of or, antibodies to, any of the above substances. Analytes may also include any antigenic substances, haptens, antibodies, macromolecules, and combinations thereof. For example, immunoassays using the disclosed devices could be adopted for antigens having known antibodies that specifically bind the antigen.

In exemplary embodiments, the disclosed devices may be used to detect the presence or absence of one or more viral antigens, bacterial antigens, fungal antigens, or parasite antigens, cancer antigens.

Exemplary viral antigens may include those derived from, for example, the hepatitis A, B, C, or E virus, human immunodeficiency virus (HIV), herpes simplex virus, Ebola virus, varicella zoster virus (virus leading to chicken pox and shingles), avian influenza virus, SARS virus, MERS virus, Epstein Barr virus, rhinoviruses, coronaviruses (such as, for example, the COVID 19 coronavirus), and coxsackieviruses.

Exemplary bacterial antigens may include those derived from, for example, *Staphylococcus aureus, Staphylococcus epidermis, Helicobacter pylori, Streptococcus bovis, Streptococcus pyogenes, Streptococcus pneumoniae, Listeria monocytogenes, Mycobacterium tuberculosis, Mycobacterium leprae, Corynebacterium diphtheriae, Borrelia burgdorferi, Bacillus anthracis, Bacillus cereus, Clostridium botulinum, Clostridium difficile, Salmonella typhi, Vibrio chloerae, Haemophilus influenzae, Bordetella pertussis, Yersinia pestis, Neisseria gonorrhoeae, Treponema pallidum, Mycoplasm sp., Legionella pneumophila, Rickettsia typhi, Chlamydia trachomatis, Shigella dysenteriae,* and *Vibrio cholera.*

Exemplary fungal antigens may include those derived from, for example, *Tinea pedis, Tinea corporus, Tinea cruris, Tinea unguium, Cladosporium carionii, Coccidioides immitis, Candida sp., Aspergillus fumigatus,* and *Pneumocystis carinii.*

Exemplary parasite antigens include those derived from, for example, *Giardia lamblia, Leishmania sp., Trypanosoma sp., Trichomonas sp.,* and *Plasmodium sp.*

Exemplary cancer antigens may include, for example, antigens expressed, for example, in colon cancer, stomach cancer, pancreatic cancer, lung cancer, ovarian cancer, prostate cancer, breast cancer, liver cancer, brain cancer, skin cancer (e.g., melanoma), leukemia, lymphoma, or myeloma.

In other embodiments, the assay reagents may react with one or more metabolic compounds. Exemplary metabolic compounds include, for example, proteins, nucleic acids, polysaccharides, lipids, fatty acids, amino acids, nucleotides, nucleosides, monosaccharides and disaccharides. For example, the assay reagent is selected to react to the presence of at least one of glucose, protein, fat, vascular endothelial growth factor, insulin-like growth factor 1, antibodies, and cytokines.

Figure 2A:
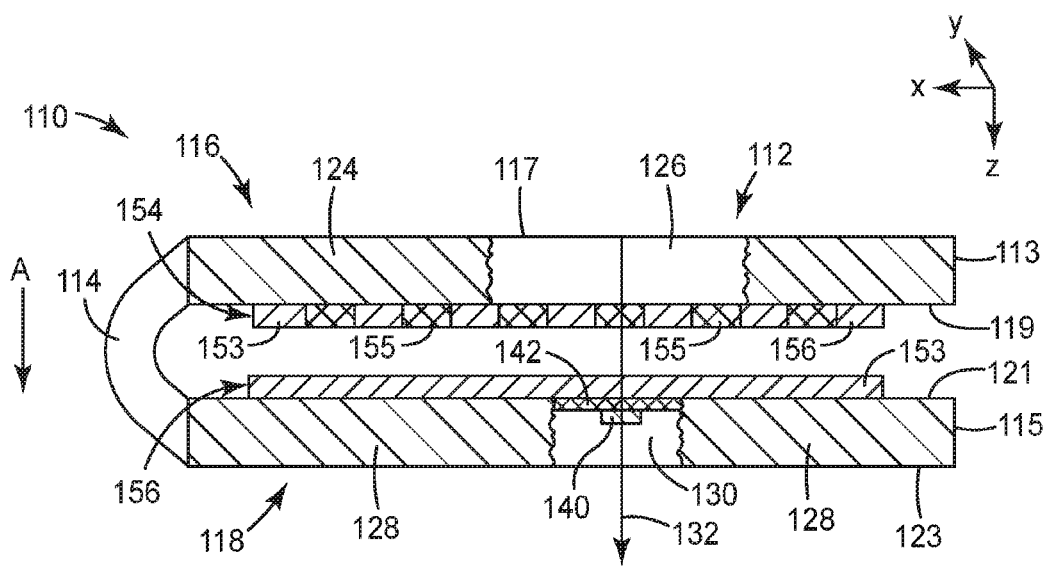
FIG. 2A is a schematic cross-sectional view of an embodiment of a diagnostic device according to the present disclosure.
Figure 2B:
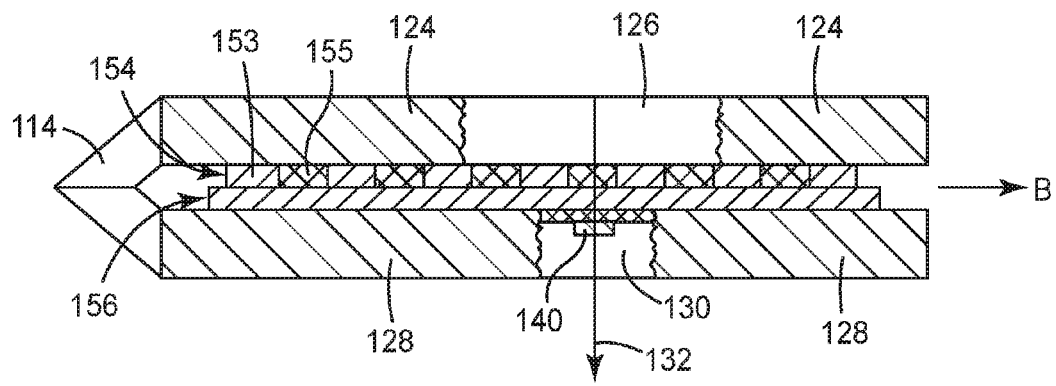
FIG. 2B is a schematic cross-sectional view of an embodiment of a diagnostic device according to the present disclosure.

Referring now to FIGS. 2A-2B, another embodiment of a diagnostic device 110 includes an elongate substantially planar hydrophilic substrate 112 with a first end 113, a second end 115, and at least one folded region 114 between the first and the second ends 113, 115. The folded region 114 separates the hydrophilic substrate 112 into a first sheet-like portion 116 and a second sheet-like portion 118, each occupying a substantially parallel plane with respect to the folded region 114. The first substrate portion 116 includes a first major surface 117 and a second major surface 119, while the second substrate portion 118 includes a first major surface 121 and a second major surface 123. In the embodiment of FIG. 2A, the first portion of the substrate 116 and the second portion of the substrate 118 overlie one another such that the respective major surfaces 119 and 121 are adjacent to each other.

The first substrate portion 116 includes a first hydrophobic region 124 and a first hydrophilic region 126, while the second substrate portion 118 includes a second hydrophobic region 128 and a second hydrophilic region 130. The hydrophobic regions 124, 128 each resist fluid flow along the direction of the arrow A, which is aligned along thickness of the substrate portions 116, 118, or along the z-axis of the three-dimensional diagnostic device 110. The hydrophilic regions 126, 130 are aligned in registration with each other such that a fluid sample placed on the first hydrophilic region 126 (not shown in FIG. 2A) can flow using, for example, wicking or capillary action, along a sample flow path 132 to provide fluid communication between the first substrate portion 116 and the second substrate portion 118 such that the fluid sample wicks into the second hydrophilic region 130.

All or a portion of one or both of the hydrophilic regions 126, 130 can include a test area 142 where an analytical result or output of the diagnostic device 110 can be displayed for a user, as well as one or more reagents 140 in the test area 142 or in fluid communication with the test area 142. The one or more reagents 140 disposed in the sample flow path 132 are selected to provide an indication of at least one of a presence, absence or concentration of an analyte in the sample fluid. In various embodiments, the reagent 140 is applied to all or a portion of one or both of the hydrophilic regions 126, 130, can be in another portion of the device 110 and in fluid communication with the flow path 132, or can be applied to the sample flow path 132 before or after the application of the fluid sample to the sample flow path 132.

Figure 2C:
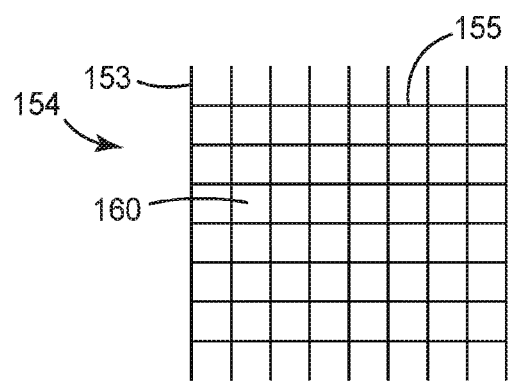
FIG. 2C is a schematic overhead view of an embodiment of a patterned adhesive suitable for use in a diagnostic device of the present disclosure.

The diagnostic device 110 includes regular or irregular grid or mesh-like first connection region 154 on the second major surface 119 of the first substrate portion 116. As shown schematically in the example embodiment of FIG. 2C, the first connection region 154 includes grid lines 153, 155 aligned substantially normal to each other.

In some embodiments, the diagnostic device 110 further includes an optional grid or mesh-like second connection region 156 on the first major surface 121 of the second substrate portion 118.

The grid-like connection regions 154, 156 are configured to include sufficient open areas 160 between the grid lines 153, 155 to allow a sample fluid to wick and flow from the first hydrophilic region 126 to the second hydrophilic region 130 along the sample flow path 132, while adhering the first substrate portion 116 to the second substrate portion 118 and maintaining the registration of the hydrophilic regions 126, 130 to preserve the alignment of the sample flow path 132 (FIG. 2B). The grid lines 153, 155 in the connection regions 154, 156, along with the hydrophobic regions 124, 128, prevent flow of the sample fluid along the direction B normal to the direction A of the sample flow path 132.

In various embodiments, the connection regions 154, 156 can include any type of adhesive described above such as, for example, pressure sensitive adhesives, hot-melt adhesives, cohesive adhesives, and the like. In some embodiments, the adhesive can be applied by spraying, printing, or use of a transfer adhesive, which provide a sufficiently open structure to allow wicking of the sample fluid between layers or panels of the device.

Figure 3A:
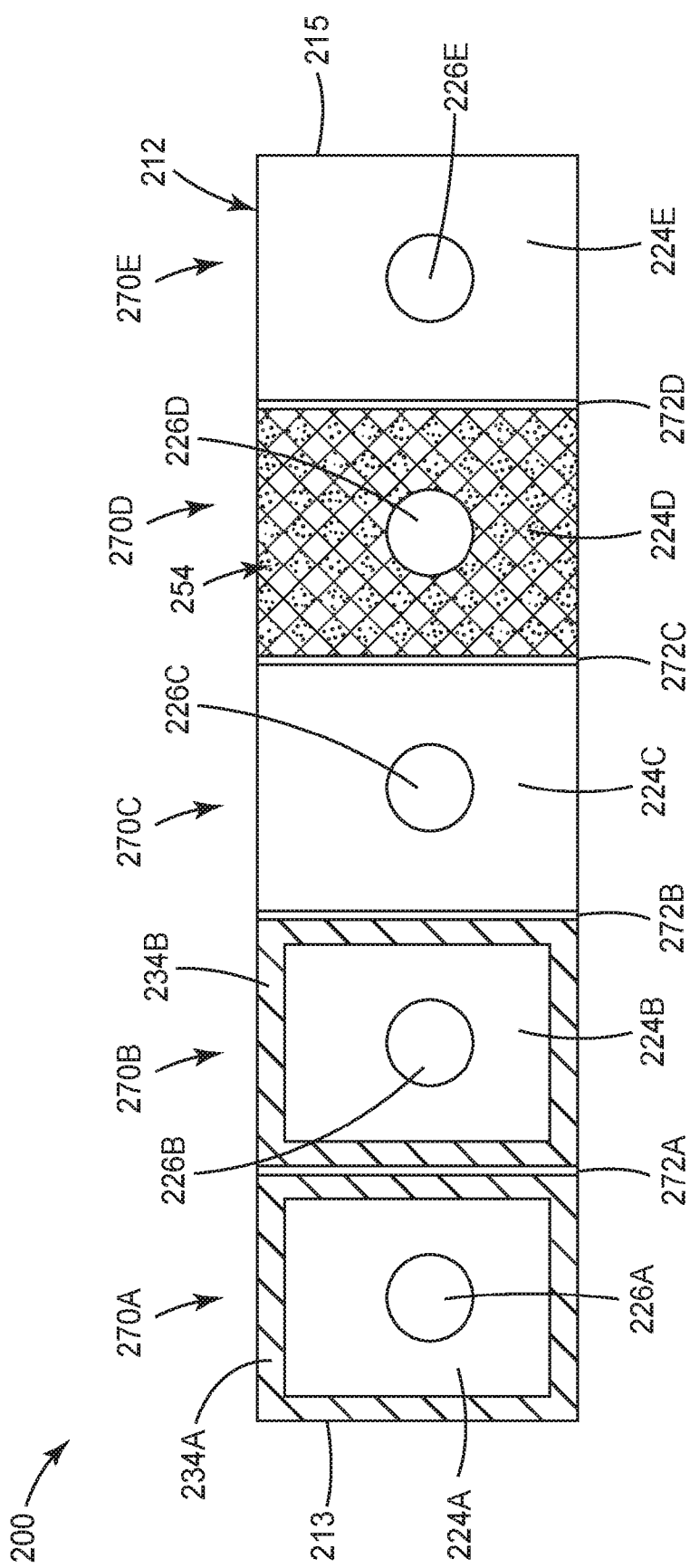
FIG. 3A is a schematic overhead view of a diagnostic device of the present disclosure.

Referring now to FIG. 3A, a portion of an elongate web 200 includes a hydrophilic substrate 212 including a first end 213 and a second end 215. The web 200 includes a plurality of web regions 270A-270E, which are separated by separation regions 272A-272D. In the embodiment of FIG. 3A, each web region 270A-270E includes a hydrophobic region 224A-224E and a hydrophilic region 226A-226E. In some embodiments, the separation regions 272 are free of the hydrophobic regions, but such an arrangement is not required. In the embodiment of FIG. 3A, the hydrophobic regions 224A-224E and the hydrophilic regions 226A-226E have the same shape, but in some embodiments the hydrophobic regions and hydrophilic regions can have different shapes, depending on the requirements of a specific diagnostic assay.

In the embodiment of FIG. 3A, the web regions 270A and 270B further include connective regions 234A, 234B that surround the hydrophilic regions 226A, 226B. In addition, in the embodiment of FIG. 3A, the web region 270D includes a patterned connective region 254 of, for example, a pressure sensitive adhesive (PSA).

As shown in FIG. 3B, the web 200 of FIG. 3A may be folded along the separation regions 272A-D in the direction of the arrows C to form a diagnostic device 300 including overlying and substantially parallel panels 270A-270E. When so folded, the connection regions 234A and 234B come together to adhere and maintain registration of the panels 270A-270B, and the patterned connective region 254 maintains the registration of the panels 270C-270D. The registration of the panels 270A-270E maintains alignment of the hydrophilic regions 226A-226E, which allows flow of sample fluid along a sample flow path 232 through the hydrophilic regions 226A-226E. While not shown in FIGS. 3A-3B, additional connective regions of any suitable shape or configuration may be used to maintain alignment of the hydrophilic regions in the panels 270B-C and 270D-E. In some embodiments, mechanical fasteners (not shown in FIGS. 3A-3B) may also be used, alone or in combination with adhesive connective regions, to maintain alignment of any or all of the panels 270A-270E.

As noted above, one or more reagents (not shown in FIG. 3B) may be included in any or all of the hydrophilic regions 226A-226E (FIG. 3A), and one or more of the panels 270A-270E may include a test area to indicate at least one of the presence, the absence, or the concentration of an analyte in a sample fluid.

In some embodiments (not shown in FIGS. 3A-3B), each web region 270A-270E may be printed on a separate web or area of a web. After the web is further processed, the individual web regions 270-270E may then be aligned, placed over each other in a desired order, and stacked to form a suitable diagnostic device. However, in some cases the alignment and stacking steps in such a process may increase the overall manufacturing cost of the diagnostic device compared to the folding process described in FIGS. 3A-3B.

In yet another aspect, the present disclosure is directed to assay methods including any of the embodiments of the diagnostic devices shown above. With reference to the diagnostic device 10 shown in FIGS. 1A-1B, example assay methods include adding a fluid sample including an analyte to the hydrophilic regions 26, 30 such that the sample fluid enters and wicks along the sample flow path 32 by capillary action. In some embodiments, water or a buffer may also be added to the hydrophilic regions 26, 32 to assist in the movement of the sample fluid along the sample flow path 32.

Visual or machine examination of the test area 42 within the hydrophilic regions 26, 30, or over the entire hydrophilic regions 26, 30, permits determination of at least one of a presence, absence, or concentration of the analyte in the fluid sample. For example, in some embodiments, the assay protocol produces a color reaction, which includes the development of a grey scale from black to white, and the examination of the development of or, intensity of, the color in the test area 42 within the hydrophilic regions 26, 30, or within the entire hydrophilic regions 26, 30, to determine the presence, absence, or concentration of the analyte.

In one embodiment, an ELISA test may be conducted using the disclosed device. The method may include the steps of: (1) addition of a sample to the device, wherein the sample is wicked directly through the hydrophilic regions 26, 30 along the sample flow path 32; (2) binding an analyte with a labeled antibody along the flow path 32 and into the test area 42; and binding the analyte binds to an antigen in the test area 42; and optionally washing the hydrophilic regions 26, 30 with a buffer such as, for example, PBS, to observe the results in the test area 42.

In another aspect, the present disclosure is directed to a kit including the diagnostic device 10 and other equipment useful in performing an assay for a selected analyte. For example, the kit may optionally include one or more vials of purified water and/or buffer, e.g., PBS, one or vials of a suitable reagent, a device to obtaining a blood sample (e.g., a device of making a needle stick), a device for collecting a urine sample or saliva sample or other body fluid, or a pipette for transferring water and/or buffer to the device. Further, the kit may include instructions or color charts for quantitating a color reaction.

The devices and methods of the present disclosure will now be further described in the following non-limiting examples.

EXAMPLES

Example 1

A flexographic ink (9418 obtained from NAZDAR Ink Technologies of Shawnee, KANS) was printed on a WHATMAN Grade 1 filter (obtained from GE Healthcare Life Sciences of Piscataway, NJ) paper substrate busing a FLEXIPROOF 100 printing system (obtained from RK Industries, Herts, United Kingdom). Printing was accomplished by using a 38.75 micrometer (25 billions of cubic microns (BCM)), 35.4 lines per centimeter (90 lines per inch) anilox roll to form a 5.08 cm (2 inch) diameter circle. After printing, the printed paper sample was heated for eight minutes at 177° C. (350° F.) and the ink was cured by exposure to UV radiation by a FUSION High Intensity UV curing system (obtained from FUSION UV Systems Inc of Hampshire, United Kingdom) outfitted with an H-bulb and conveyed at 1.5 meters (5 feet) per minute to form a hydrophobic region on the paper sample. After curing, the printed paper sample was tested for performance by depositing dyed deionized water into non-printed areas and visually inspecting the spread of the dyed water. The dye was added to water to help with observations.

Figure 4A:
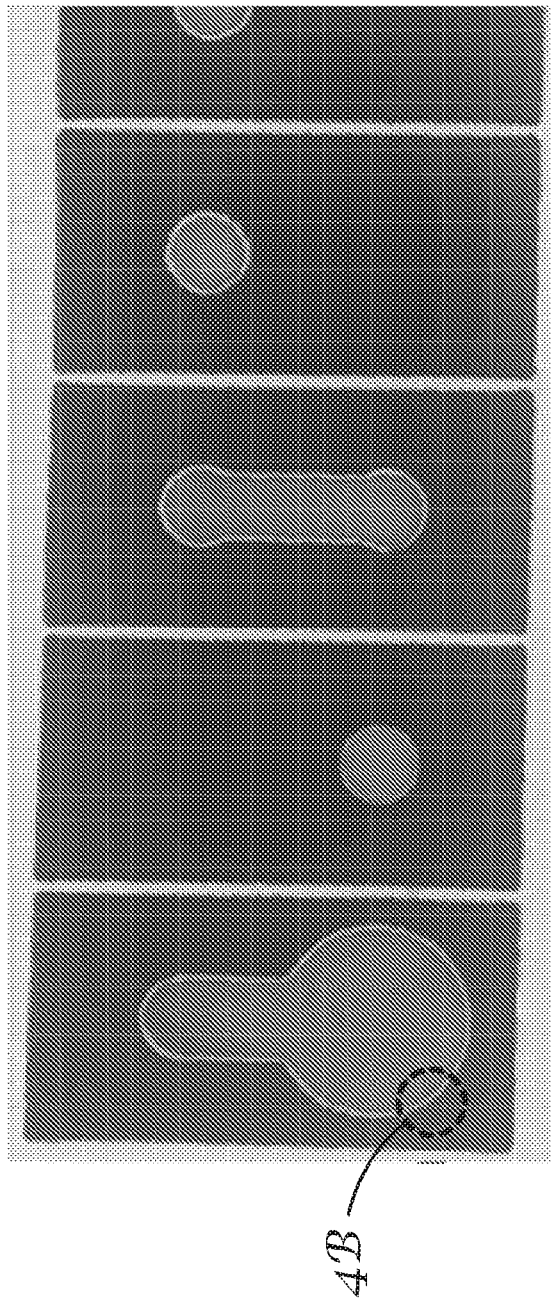
FIG. 4A is an overhead view of a border around a printed hydrophobic region of Example 1 that formed due to wicking of components of printed materials in lateral direction.
Figure 4B:
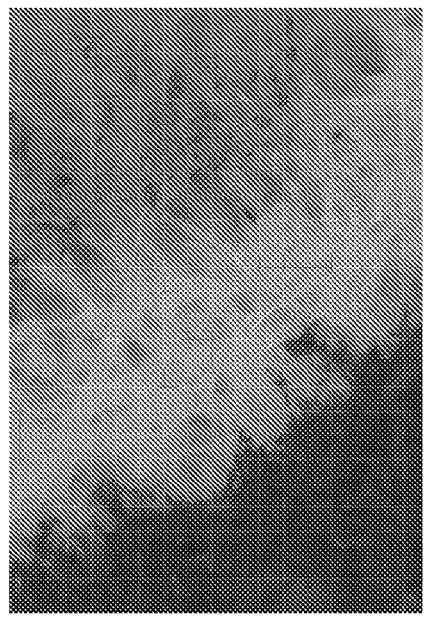
FIG. 4B is a magnified sectional view of the diagnostic device of Example 1 and FIG. 4A.

FIGS. 4A-4B show images of the printed paper after testing with dyed water. The dyed water saturated most of the unprinted area but did not wick into the printed areas as well as into the areas close to the border of the printed areas. This ink has pigment particulates in it (they show as blue), that did not wick along the fibers, while polymer component of the ink did, creating hydrophobic areas around printed pattern. Grey-colored water stopped at the created hydrophobic border.

A test was performed to show that volumetrically hydrophobic areas of the paper retained sufficient fluid permeability. A 5.08 cm (2 inch) dimeter round disc was cut out of the printed paper. The paper samples were inserted into a standard filter housing and a water line with one meter of head pressure was connected to the filter housing and outflow was measured. Refer to Table 1 below and FIG. 5 for test results.

TABLE 1

| Sample | Average Flow Rate (ml/sec) |
| --- | --- |
| Control | 4.56 |
| 100% Easy Release | 2.36 |
| 80% Easy Release | 2.24 |
| 60% Easy Release | 2.08 |
| NAZDAR 9418 | 1.70 |
| NAZDAR 1028 | 1.90 |
| Wax | 0.23 |

Example 2

A sample was created as described in Example 1 using OP 1028 ink (obtained from NAZDAR Ink Technologies of Shawnee, KANS) instead of the 9418 ink. A test was performed to show that volumetrically hydrophobic areas of the printed paper retained sufficient fluid permeability. A 5.08 cm (2 inch) dimeter round disc was cut out of the printed paper. The paper samples were inserted into a standard filter housing and a water line with one meter of head pressure was connected to the filter housing and outflow was measured. Refer to Table 1 and FIG. 5 for test results.

Examples 3 – 5

Three samples were created as described in Example 1 using a release ink UVF03408 (UV Easy Release) (obtained from FlintGroup, Rogers, MN) instead of the 9418 ink. The first sample was undiluted. Before applying the ink, the second sample diluted the release ink by adding 20 percent isopropyl alcohol (IPA) solvent Before applying the ink, the third sample diluted the release ink by adding 40 percent IPA solvent. Samples with the solvent-containing ink were dried at room temperature for 15 minutes. A test was performed to show that volumetrically hydrophobic areas of the printed paper retained sufficient fluid permeability. A 5.08 cm (2 inch) dimeter round disc was cut out of the printed paper. The paper samples were inserted into a standard filter housing and a water line with one meter of head pressure was connected to the filter housing and outflow was measured. Refer to Table 1 and FIG. 5 for test results.

Comparative Example 1

A wax-saturated paper was made by melting Batik Wax (available from Jacquard Products, Healdsburg, CA) at 65.6° C. (150° F.) and dripping it on WHATMAN Grade 1 paper preheated to the same temperature until saturation of less than about 5 minutes. A test was performed to show that volumetrically hydrophobic areas of the printed paper retained sufficient fluid permeability. A 5.08 cm (2 inch) dimeter round disc was cut out of the printed paper. The paper samples were inserted into a standard filter housing and a water line with one meter of head pressure was connected to the filter housing and outflow was measured. Refer to Table 1 and FIG. 5 for test results.

Example 6

A CH 265 self-adhering adhesive (obtained from Valpac Industries, Federalsburg, MD) was manually applied by a cotton swab onto the printed regions on both sides of the sample created in Example 1. After drying at room temperature for one hour, the sample was folded and lightly pressed together. Dyed water was placed on one side of the sample and wicking to the other side was observed after 25 seconds indicating that fluid transport across layers was successful.

Example 7

An adhesive was printed in an open mesh pattern onto the hydrophobic printed regions of a specific region of the configuration as described in Example 1.

Figure 5:
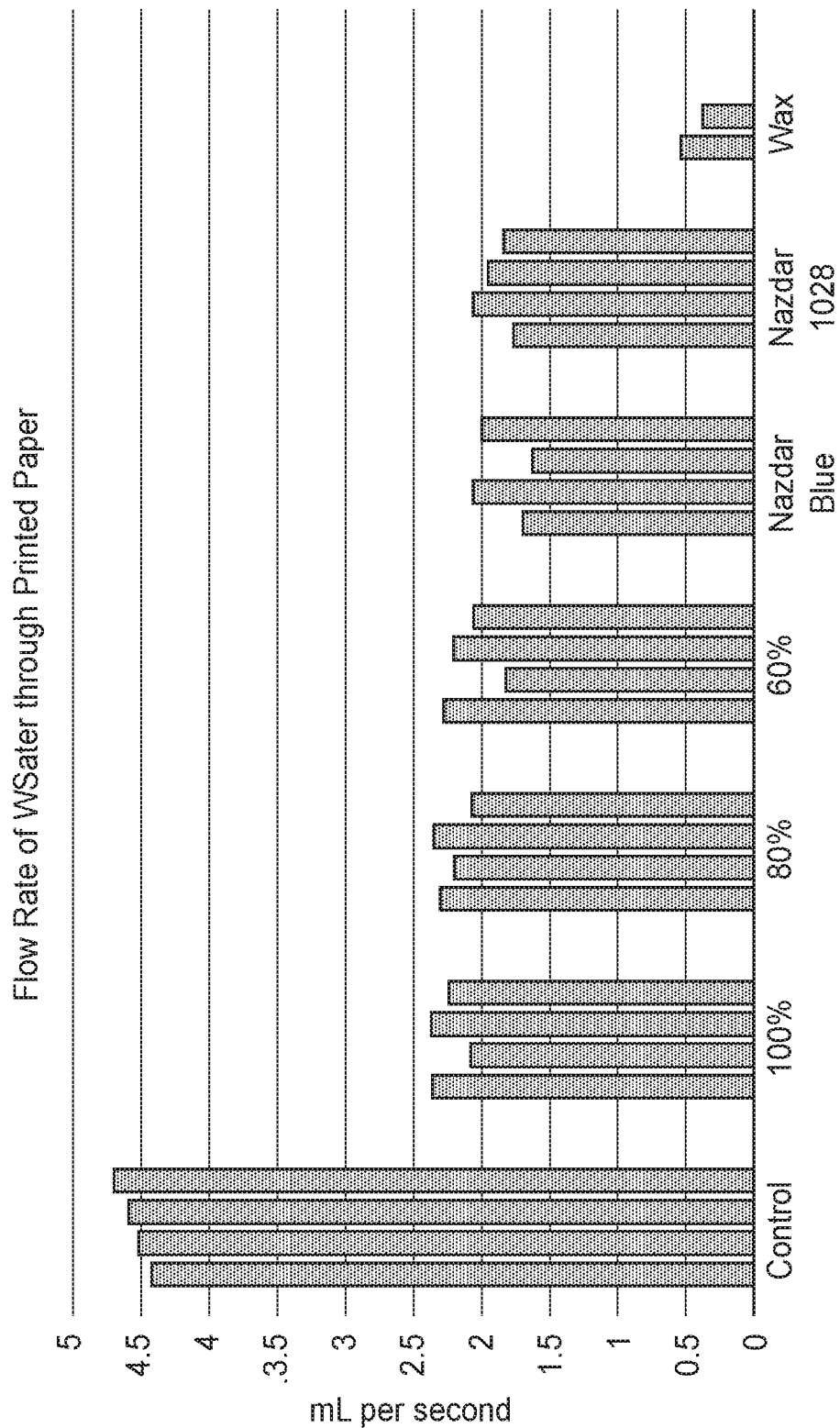
FIG. 5 is a plot of flow rate through the substrate for unpatterned hydrophilic areas and patterned hydrophobic areas of a substrate of the diagnostic device of Example 1.

Table 1 and FIG. 5 show in pertinent part that flow was highest for unprinted paper, followed by the printed paper. This shows that while printed paper remained permeable to water. Flow through wax-saturated disc was very low and was due to delamination of wax under one meter of water pressure.

Example 8

Flint Group Easy Release Coating (available from FlintGroup, Rogers, MN) was flexographically printed on a 12-wide roll of Great Lakes filter paper (equivalent to # 1 Whatman, grade 601, available from Great Lakes Filters, Bloomfield Hills, MI) on custom-made flexographic printing line using 24 bcm (billion cubic microns), 100 lines per inch anilox roll at 10 fpm line speed in a pattern representing an array of 5 folds of bio-diagnostics devices.

The ink was in-line UV cured on both sides in two passes. Single 5-fold devices were cut out of the roll of paper and folded along unprinted spaces between the prints. 3M spray adhesive (3M Spray 77, available from 3M Company) was lightly sprayed by hand on both side of the device over both hydrophobic and hydrophilic areas.

After drying for 2 minutes, device was folded. Dyed water was placed on the top hydrophilic circle (covered with sprayed adhesive) and left to wick. Wicking to the other side was observed in about 50 seconds indicating that fluid transport across layers was successful.

Various embodiments of the invention have been described. These and other embodiments are within the scope of the following claims.

The invention claimed is:

1. A diagnostic device, comprising:
an elongate substantially planar porous substrate with a first end and a second end, wherein the substrate comprises at least one folded region between the first end and the second end, and wherein:
a first portion of the substrate lies in a first plane with respect to the folded region, wherein the first portion of the substrate comprises a first hydrophobic region and a first hydrophilic region, wherein the first hydrophobic region comprises a first low surface energy polymeric material extending from a first major surface of the first portion of the substrate to a second major surface of the first portion of the substrate, and wherein the first hydrophobic region comprises an arrangement of interconnected open pores providing at least one uninterrupted path extending from the first major surface of the first portion of the substrate to the second major surface of the first portion of the substrate; and
a second portion of the substrate that lies in a second plane with respect to the folded region, wherein the second plane is substantially parallel to the first plane, the second portion of the substrate comprising a second hydrophilic region and a second hydrophobic region comprising a second low surface energy polymeric material, which may be the same or different from the first low surface energy polymeric material, extending from a first major surface of the second portion of the substrate to second major surface of the second portion of the substrate, and wherein the second hydrophobic region comprises an arrangement of interconnected open pores providing at least one uninterrupted path extending from the first major surface of the second portion of the substrate to the second major surface of the second portion of the substrate;
at least one connective region between the first portion of the substrate and the second portion of the substrate, wherein the at least one connective region is configured to maintain alignment of the first hydrophilic region and the second hydrophilic region sufficient to provide a sample flow path between the first portion of the substrate and the second portion of the substrate along a direction normal to the first plane and the second plane; and
a reagent along the sample flow path, wherein the reagent is selected to detect at least one of a presence, an absence or a concentration of an analyte present in a sample applied to the diagnostic device.

2. The diagnostic device of claim 1, wherein the at least one connective region comprises a layer of an adhesive chosen from a pressure sensitive adhesive, a hot-melt adhesive, a cohesive adhesive, and mixtures and combinations thereof.

3. The diagnostic device of claim 2, wherein the at least one connective region comprises a patterned adhesive on at least one of the first portion of the substrate and the second portion of the substrate, wherein the patterned adhesive comprises an arrangement of open regions configured to allow flow of a fluid between the first hydrophilic region of the first portion of the substrate and the second hydrophilic region of the second portion of the substrate.

4. The diagnostic device of claim 1, wherein the elongate porous substrate is chosen from paper, nonwoven materials, polymeric films, and combinations thereof.

5. The diagnostic device of claim 1, wherein the first and the second low surface energy polymeric materials each comprise a radiation curable polymeric ink.

6. The diagnostic device of claim 1, wherein the first and the second low surface energy polymeric materials comprise monomers, oligomers, or polymers chosen from fluorocarbons, silicones, or hydrocarbons.

7. The diagnostic device of claim 1, wherein the first and the second low surface energy polymeric materials comprise a hydrophobic ink with a surface energy lower than 35 dynes/cm.

8. A kit comprising the diagnostic device of claim 1 and a sample collection apparatus configured to collect a sample comprising the analyte.

9. A diagnostic device, comprising:
an elongate substantially planar porous fibrous substrate with a first end and a second end, wherein the substrate comprises:
a plurality of folded regions between the first end and the second end, the plurality of folded regions dividing the planar porous substrate into a stack of overlying substantially planar panels, wherein each of the panels in the stack occupies a different substantially parallel plane, and wherein each of the panels comprises:
a hydrophobic area comprising fibers coated with a hydrophobic low surface energy polymeric ink such that open areas remain between the fibers, the open areas between the fibers providing at least one uninterrupted open path between a first major surface of the panel and a second major surface of the panel, and a hydrophilic area; and wherein at least some of the panels comprise:
a reagent selected to detect an analyte present in a sample, and
a connective region configured to attach adjacent panels to each other; and
wherein the hydrophobic areas and hydrophilic areas in adjacent panels of the stack are aligned with each other to provide a sample flow path between the hydrophilic areas thereof along a direction normal to the first plane and the second plane such that the sample contacts the reagent disposed in the flow path to provide an indication of at least one of the presence, absence or concentration of the analyte in the sample.

10. The diagnostic device of claim 9, wherein the connective region comprises an adhesive chosen from a pressure sensitive adhesive, a hot melt adhesive, a cohesive adhesive, and mixtures and combinations thereof.

11. The diagnostic device of claim 9, wherein adjacent overlying panels comprise registered areas of a cohesive adhesive configured to allow fluid flow between the hydrophilic areas in adjacent panels.

12. The diagnostic device of claim 9, wherein the connective region comprises a patterned adhesive comprising an arrangement of open regions, the open regions configured to allow flow of a fluid between adjacent panels.

13. The diagnostic device of claim 9, wherein the connective region occupies a periphery of the panels and surrounding the hydrophobic layer.

14. The diagnostic device of claim 9, wherein the hydrophobic areas surround the hydrophilic areas.

15. The diagnostic device of claim 9, wherein the elongate porous substrate is chosen from paper, nonwoven materials, polymeric films, and combinations thereof.

16. The diagnostic device of claim 9, wherein the ink is radiation curable.

17. A system, comprising:
a diagnostic device, comprising:
an elongate substantially planar porous substrate with a first end and a second end, wherein the substrate comprises at least one folded region between the first end and the second end, and wherein:
a first portion of the substrate lies in a first plane with respect to the folded region, wherein the first portion of the substrate comprises a first hydrophobic region and a first hydrophilic region, wherein the first hydrophobic region comprises a hydrophobic polymeric low surface energy material extending from a first major surface of the first portion of the substrate to a second major surface of the first portion of the substrate, and wherein the first hydrophobic region comprises an arrangement of interconnected open pores providing at least one uninterrupted path extending from the first major surface of the first portion of the substrate to the second major surface of the first portion of the substrate; and
a second portion of the substrate, different from the first portion of the substrate, wherein the second portion of the substrate lies in a second plane with respect to the folded region, wherein the second plane is substantially parallel to the first plane, the second portion of the substrate comprising a second hydrophilic region and a second hydrophobic region comprising the hydrophobic polymeric low surface energy material and extending from a first major surface of the second portion of the substrate to second major surface of the second portion of the substrate, and wherein the second hydrophobic region comprises an arrangement of interconnected open pores providing at least one uninterrupted path extending from the first major surface of the second portion of the substrate to the second major surface of the second portion of the substrate;
at least one connective region between the first portion of the substrate and the second portion of the substrate, wherein the at least one connective region is configured to maintain registration of the first hydrophilic region and the second hydrophilic region sufficient to provide a passive sample flow path between the first portion of the substrate and the second portion of the substrate along a direction normal to the first plane and the second plane; and
a reagent selected to detect at least one of a presence, an absence or a concentration of an analyte present in a sample fluid applied to flow path of the diagnostic device.

18. The system of claim 17, wherein the at least one connective region comprises an adhesive chosen from a pressure sensitive adhesive, a hot-melt adhesive, a cohesive adhesive, and mixtures and combinations thereof.

19. The system of claim 17, wherein the at least one connective region comprises a mechanical fastener.

20. The system of claim 19, wherein the mechanical fastener is chosen from staples, clips, elastic bands, zip ties, and combinations thereof.

* * * * *